United States Patent
Freund et al.

(10) Patent No.: US 10,004,689 B2
(45) Date of Patent: Jun. 26, 2018

(54) NANOPARTICLE COMPOSITIONS FOR GENERATION OF REGULATORY T CELLS AND TREATMENT OF AUTOIMMUNE DISEASES AND OTHER CHRONIC INFLAMMATORY CONDITIONS

(71) Applicant: TOPAS THERAPEUTICS GmbH, Hamburg (DE)

(72) Inventors: Barbara Freund, Hamburg (DE); Jörg Heeren, Hamburg (DE); Peter Nielsen, Besitz (DE); Antonella Carambia, Hamburg (DE); Johannes Herkel, Hamburg (DE); Oliver Bruns, Boston, MA (US); Ansgar Lohse, Hamburg (DE); Stefan Lüth, Hamburg (DE); Horst Weller, Hamburg (DE); Sunhild Salmen, Hamburg (DE)

(73) Assignee: TOPAS THERAPEUTICS GmbH, Hamburg (DE)

( * ) Notice: Subject to any disclaimer, the term of this patent is extended or adjusted under 35 U.S.C. 154(b) by 307 days.

(21) Appl. No.: 13/261,883

(22) PCT Filed: Nov. 14, 2012

(86) PCT No.: PCT/EP2012/004735
§ 371 (c)(1),
(2) Date: May 14, 2014

(87) PCT Pub. No.: WO2013/072051
PCT Pub. Date: May 23, 2013

(65) Prior Publication Data
US 2014/0294982 A1 Oct. 2, 2014

(30) Foreign Application Priority Data
Nov. 14, 2011 (EP) .................................. 11009032

(51) Int. Cl.
| | |
|---|---|
| *A61K 9/14* | (2006.01) |
| *A61K 9/107* | (2006.01) |
| *A61K 49/00* | (2006.01) |
| *A61K 49/18* | (2006.01) |
| *A61K 51/12* | (2006.01) |
| *A61K 39/00* | (2006.01) |
| *A61K 39/39* | (2006.01) |
| *C12N 5/0783* | (2010.01) |
| *A61K 47/69* | (2017.01) |
| *A61K 9/00* | (2006.01) |

(52) U.S. Cl.
CPC ............ *A61K 9/146* (2013.01); *A61K 9/1075* (2013.01); *A61K 39/0008* (2013.01); *A61K 39/39* (2013.01); *A61K 47/6907* (2017.08); *A61K 49/0067* (2013.01); *A61K 49/1809* (2013.01); *A61K 49/1857* (2013.01); *A61K 51/1227* (2013.01); *C12N 5/0637* (2013.01); *A61K 9/0019* (2013.01); *A61K 2039/55555* (2013.01); *C12N 2502/14* (2013.01)

(58) Field of Classification Search
None
See application file for complete search history.

(56) References Cited

U.S. PATENT DOCUMENTS

| | | |
|---|---|---|
| 2010/0069550 A1 | 3/2010 | Gao et al. |
| 2011/0054236 A1 | 3/2011 | Yang et al. |

FOREIGN PATENT DOCUMENTS

| | | |
|---|---|---|
| EP | 2226634 A2 | 9/2010 |
| EP | 2255831 A1 | 12/2010 |
| WO | 2009/067349 | 5/2009 |
| WO | 2009/126835 A2 | 10/2009 |
| WO | 2013/072051 A1 | 5/2013 |

OTHER PUBLICATIONS

International Search Report from corresponding International Application No. PCT/EP2012/004735, dated Nov. 14, 2012 (5 pages).
International Preliminary Report on Patentability from corresponding International Application No. PCT/EP2012/004735, dated May 20, 2014 (8 pages).
Hogquist, K.A., Baldwin, T.A., and Jameson, S.C. 2005. Central tolerance: learning self-control in the thymus. Nat. Rev. Immunol. 5: 772-782 (11 pages).
Goodnow, C.C., Sprent, J., Fazekas de St Groth, B., and Vinuesa, C.G. 2005. Cellular and genetic mechanisms of self tolerance and autoimmunity. Nature. 435: 590-597 (8 pages).
Jonuleit, H., and Schmitt, E. 2003. The regulatory T cell family: distinct subsets and their interrelations. J. Immunol. 171: 6323-6327 (5 pages).
Viglietta, V., Baecher-Allan, C., Weiner, H.L., and Hafler, D.A. 2004. Loss of functional suppression by CD4+CD25+ regulatory T cells in patients with multiple sclerosis. J. Exp. Med.199: 971-979 (9 pages).
Von Herrath, M.G., and Harrison, L.C. 2003. Antigen-induced regulatory T cells in autoimmunity. Nat. Rev. Immunol. 3: 223-32 (10 pages).
Fontenot, J.D., Gavin, M.A., and Rudensky, A.Y. 2003. Foxp3 programs the development and function of CD4+CD25+ regulatory T cells. Nat. Immunol. 4: 330-336 (7 pages).
(Continued)

*Primary Examiner* — Yunsoo Kim
(74) *Attorney, Agent, or Firm* — Hovey Williams LLP

(57) ABSTRACT

The present invention relates to nanoparticles for the targeted delivery of antigen to liver cells, in particular, liver sinusoidal endothelial cells (LSEC) and/or Kupffer cells, and for the in vivo generation of regulatory T cells, notably CD4+CD25+FOXP3+ regulatory T cells (Treg). The invention provides pharmaceutical compositions and methods for the prevention and treatment of autoimmune diseases, allergies or other chronic inflammatory conditions, and for generation of regulatory T cells. The nanoparticles used in the invention comprise a) a micelle comprising an amphiphilic polymer rendering the nanoparticle water-soluble, and b) a peptide comprising at least one T cell epitope associated with the outside of the micelle. The micelle may or may not comprise a solid hydrophobic core.

16 Claims, 12 Drawing Sheets

(56) References Cited

OTHER PUBLICATIONS

Figure 1:
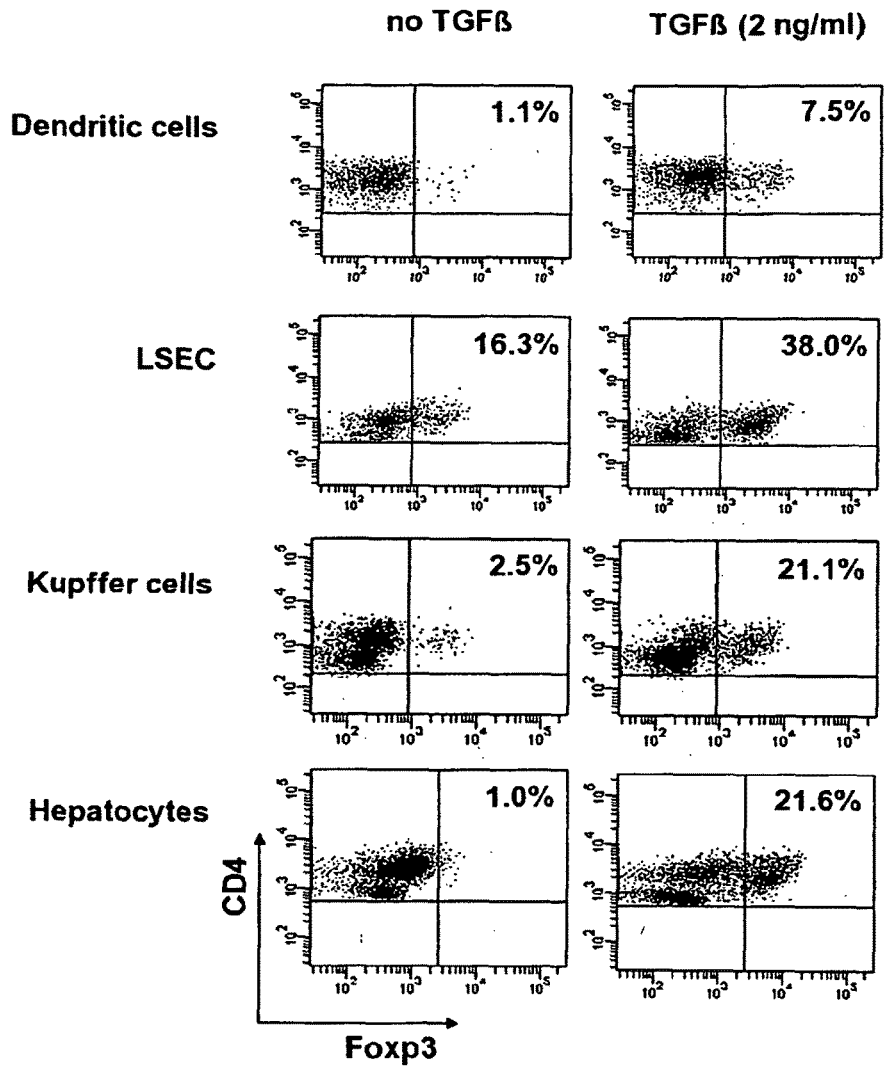

Sakaguchi, S. 2005. Naturally arising Foxp3-expressing CD25+CD4+ regulatory T cells in immunological tolerance to self and non-self. Nat. Immunol. 6: 345-352 (8 pages).
Wan, Y.Y., and Flavell, R.A. 2006. The roles for cytokines in the generation and maintenance of regulatory T cells. Immunol. Rev. 212: 114-130 (17 pages).
Huber, S., and Schramm, C. 2006. TGF-beta and CD4+CD25+ regulatory T cells. Front. Biosci. 11: 1014-1023 (10 pages).
Shevach, E.M. 2009. Mechanisms of Foxp3+ T regulatory cell-mediated suppression. Immunity 30: 636-645 (10 pages).
Von Boehmer, H. 2005. Mechanisms of suppression by suppressor T cells. Nat. Immunol. 6: 338-344 (7 pages).
Gavin, M.A., Clarke, S.R., Negrou, E., Gallegos, A., and Rudensky, A. 2002. Homeostasis and anergy of CD4+CD25+ suppressor T cells in vivo. Nat. Immunol. 3: 33-41 (9 pages).
Walker, L.S., Chodos, A., Eggena, M., Dooms, H., and Abbas, A.K. 2003. Antigen-dependent proliferation of CD4+CD25+ regulatory T cells in vivo. J. Exp. Med. 198: 249-258 (10 pages).
Liang, S., et al. 2005. Conversion of CD4+ CD25− cells into CD4+ CD25+ regulatory T cells in vivo requires B7 costimulation, but not the thymus. J. Exp. Med. 201: 127-137 (11 pages).
Knoechel, B., Lohr, J., Kahn, E., Bluestone, J.A., and Abbas, A.K. 2005. Sequential development of interleukin 2-dependent effector and regulatory T cells in response to endogenous systemic antigen. J. Exp Med. 202: 1375-1386 (12 pages).
Kretschmer, K., et al. 2005. Inducing and expanding regulatory T cell populations by foreign antigen. Nat. Immunol. 6: 1219-1227 (9 pages).
Quintana, F.J., et al. 2008. Control of Treg and TH17 cell differentiation by the aryl hydrocarbon receptor. Nature. 453: 65-71 (8 pages).
Crispe, I.N. 2003. Hepatic T cells and liver tolerance. Nat. Rev. Immunol. 3: 51-62 (12 pages).
Limmer, A., et al. 1998. Failure to induce organ-specific autoimmunity by breaking of tolerance: importance of the microenvironment. Eur. J. Immunol. 28: 2395-2406 (12 pages).
Knolle, P.A., et al. 1999. Induction of cytokine production in naïve CD4 (+) T cells by antigen-presenting murine liver sinusoidal endothelial cells but failure to induce differentiation toward Th1 cells. Gastroenterology 116: 1428-1440 (13 pages).
Limmer, A., et al. 2000. Efficient presentation of exogenous antigen by liver endothelial cells to CD8+ T cells results in antigen-specific T cell tolerance. Nat. Med. 6: 1348-1354 (7 pages).
Calne, R.Y., et al. 1969. Induction of immunological tolerance by porcine liver allografts. Nature 223: 472-476 (5 pages).
Cantor, H.M., and Dumont, A.E. 1967. Hepatic suppression of sensitization to antigen absorbed into the portal system. Nature 215: 744-745 (2 pages).
Luth, S., et al. 2008. Ectopic expression of neural autoantigen in mouse liver suppresses experimental autoimmune neuroinflammation by inducing antigen-specific Tregs. J. Clin. Invest. 118: 3403-3410 (8 pages).
Yu, W.W., Falkner, J.C., Yavuz, C.T., and Colvin, V.L. 2004. Synthesis of monodisperse iron oxide nanocrystals by thermal decomposition of iron carboxylate salts. Chem. Commun. 20: 2306-2307 (2 pages).
Shtykova, E.V., et al. 2008. Hydrophilic monodisperse magnetic nanoparticles protected by an amphiphilic alternating copolymer, J. Phys. Chem. C 112: 16809-16817 (21 pages).
Wiegard, C., Frenzel, C., Herkel, J., Kallen, K.J., Schmitt, E., and Lohse, A.W. 2005. Murine liver antigen presenting cells control suppressor activity of CD4+CD25+ regulatory T cells. Hepatology 42:193-199 (7 pages).
Schrage, A., et al. 2008. Murine CD146 is widely expressed on endothelial cells and is recognized by the monoclonal antibody ME-9F1. Histochem. Cell. Biol. 129:441-451 (11 pages).
Wiegard, C., et al. 2007. Defective T helper 1 response by hepatocyte-stimulated CD4 T cells impairs anti-viral CD8 response and viral clearance. Gastroenterology 133: 2010-2018 (9 pages).
Huberman, A., and Perez C. 2002. Nonheme iron determination. Anal. Biochem. 307: 375-378 (4 pages).
Wu, X. et al. 2002. Immunofluorescent labeling of cancer marker Her2 and other cellular targets with semiconductor quantum dots. Nat. Biotechnol. 21: 41-46 (6 pages).
Nguyen et al., 2004, Gene Ther. 11 (Suppl 1); S76-S84 Liver gene therapy: Advances and hurdles (9 pages).
Carambia et al. 2010, J. Hepatol 52, S59-S182. Liver Sinusoidal Endothelial Cells Induce TGF-b Dependent Conversion of CD4+FOXP3+ Regulatory T Cells From Conventional CD4+CD25− T Cells (1 page).
Minchin 2008. Nature Nanotechnol. 3: 12-13. Sizing up targets with nanoparticles (2 pages).
Giri et al. 2011, Acta Biophys Sin, 1-7. Targeted novel surface-modified nanoparticles for interferon delivery for the treatment of hepatitis B (7 pages).
Shen et al. 2011, Int. J. Nanomedicine 6: 1229-1235. A role of cellular glutathione in the differential effects of iron oxide nanoparticles on antigen-specific T cell cytokine expression (8 pages).
Wu et al. 2009, Mol. Pharm. 6:1506-1517. Galactosylated LDL nanoparticles: a novel targeting delivery system to deliver antigen to macrophages and enhance antigen specific T cell responses (21 pages).
Bruns et al. 2009, Nat. Nanotechnol. 4:193-201. Real-time magnetic resonance imaging and quantification of lipoprotein metabolism in vivo using nanocrystals (9 pages).
Weiner, H.L., A. P. da Cunha, F. Quintana, H. Wu. 2011, Immunol Rev, 241: 241-259 Oral tolerance (33 pages).
Andersson, J., et al. 2008, J Exp Med 205, 1975-1981. CD4+FoxP3+ regulatory T cells confer infectious tolerance in a TGF-β-dependent manner (7 pages).
Tran, D. Q., et al. 2009, PNAS USA 106: 13445-13450. GARP (LRRC32) is essential for the surface expression of latent TGF-β on platelets and activated FOXP3+ regulatory T cells (7 pages).
Pellegrino, T, et al. 2004, Nano Letters 4: 703-707. Hydrophobic nanocrystals coated with an amphiphilic polymer shell: a general route to water soluble nanocrystals (5 pages).
Bartelt, A., et al. 2011, Nat Med 17: 200-205. Brown adipose tissue activity controls triglyceride clearance (7 pages).
Liu, George Y., et al. 1995, Immunity 3: 407-415. Low avidity recognition of self-antigen by T cells permits escape from central tolerance (9 pages).
Huber, S., et al. 2004, J Immunol 173: 6526-6531. Cutting Edge: TGF-β Signaling Is Required for the In Vivo Expansion and Immunosuppressive Capacity of Regulatory CD4+CD25+ T Cells (6 pages).
Shimizu, J., et al. 1999, J Immunol 163: 5211-5218. Induction of Tumor Immunity by Removing CD25+CD4+ T Cells: A Common Basis Between Tumor Immunity and Autoimmunity (8 pages).
Gunn Jonathan et al: "A multimodal targeting nanoparticle for selectively labeling T cells.", Small (Weinheim An Der Bergstrasse, Germany) Jun. 2008 LNKD- PUBMED:18528851, vol. 4, No. 6, Jun. 2008 (Jun. 2008), pp. 712-715 (4 pages).
Sun Conroy et al: "PEG-mediated synthesis of highly dispersive multifunctional superparamagnetic nanoparticles: their physicochemical properties and function in vivo.", ACS NANO Apr. 27, 2010 LNKD-PUBMED:20232826, vol. 4, No. 4, Apr. 27, 2010 (Apr. 27, 2010), pp. 2402-2410 (9 pages).
Cho Y S et al: "Cetuximab-conjugated magneto-fluorescent silica nanoparticles for in vivo colon cancer targeting and imaging", Cancer Letters, New York, NY, US, vol. 299, No. 1, Dec. 18, 2010 (Dec. 18, 2010), pp. 63-71 (9 pages).
Garden O A et al: "A rapid method for labelling CD4<+> T cells with ultrasmall paramagnetic iron oxide nanoparticles for magnetic resonance imaging that preserves proliferative, regulatory and migratory behaviour in vitro", Journal of Immunological Methods, Elsevier Science Publishers B.V.,Amsterdam, NL, vol. 314, No. 1-2, Jul. 31, 2006 (Jul. 31, 2006), pp. 123-133 (11 pages).
Office Action dated Jul. 29, 2016 in related European application Patent Serial No. 12 790 425.8.

3B 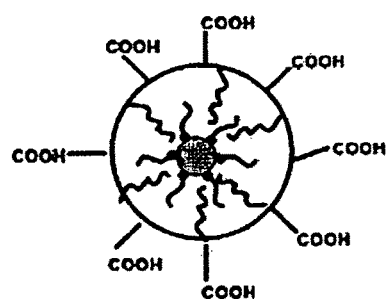
Fig. 4A
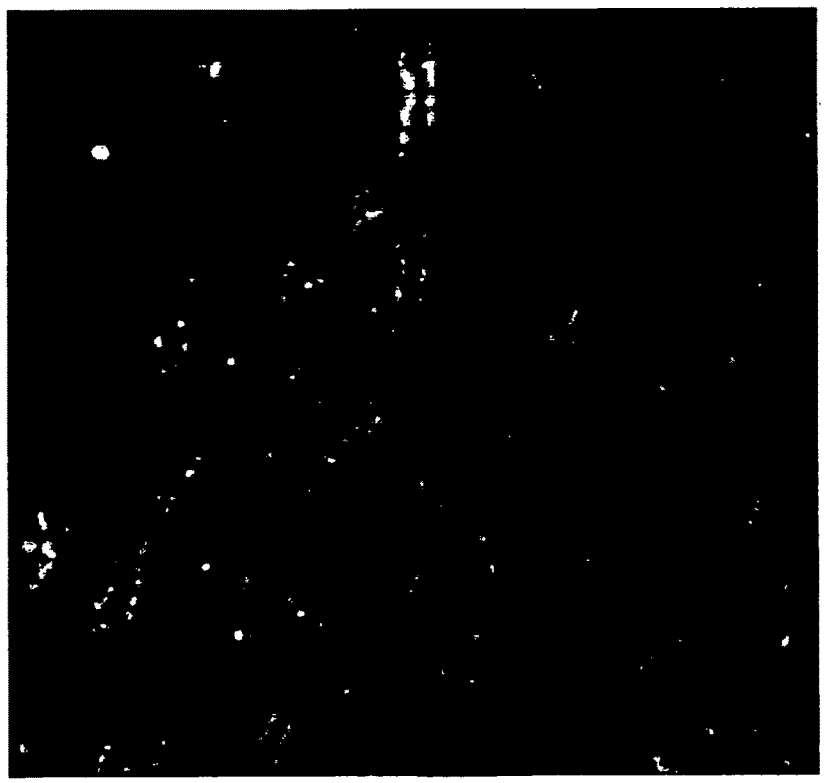

NANOPARTICLE COMPOSITIONS FOR GENERATION OF REGULATORY T CELLS AND TREATMENT OF AUTOIMMUNE DISEASES AND OTHER CHRONIC INFLAMMATORY CONDITIONS

The present, invention relates to nanoparticles for the targeted delivery of antigen to liver cells, in particular, liver sinusoidal endothelial cells (LSEC) and/or Kupffer cells, and for the in vivo generation of regulatory T cells, notably CD4+CD25+FOXP3+ regulatory T cells (Treg). The invention provides compositions and methods for the prevention and treatment of autoimmune diseases, allergies or other chronic inflammatory conditions, and for generation of regulatory T cells.

Immune tolerance to self-antigens is maintained by multiple mechanisms that control potentially pathogenic autoreactive lymphocytes, including deletion, clonal anergy or suppression by regulatory T cells (1-3). Autoimmune disease may thus result from insufficient control of autoreactive lymphocytes (4,5), and a major goal of immunotherapy for autoimmune diseases is the induction of tolerance to autoantigens by restoring regulation (6). A particularly promising way to restore self-tolerance seems to be the manipulation of autoantigen-specific $CD4^+CD25^+FOXP3^+$ regulatory T cells (Treg); adoptive transfer of these cells can prevent autoimmune or inflammatory conditions (6-10). Indeed, Treg feature several secreted or membrane-bound molecules that communicate inhibitory signals to other effector T cells, thereby suppressing proliferation and inflammatory cytokine secretion (11,12). In vivo, the majority of Treg seems to be generated in the thymus (8); however, these cells may also be generated in the periphery (9,10). Indeed, increasing evidence suggests that peripheral Treg can be generated not only by peripheral expansion of thymic Treg (13,14), but also by de novo conversion from conventional $CD4^+Foxp3^-$ T cells (15-18). So far, however, it is not clear, how the therapeutic potential of specific Treg generation in the periphery could be effectively translated into clinically applicable therapies.

The microenvironment of the liver favours immune tolerance, presumably by a combination of tolerogenic antigen presenting cells and cytokines (19-22). Thus, in many situations, the outcome of T cell stimulation by liver cells is immune tolerance. Such hepatic tolerance induction may not only function locally in the liver, but also systemically. Indeed, it has been shown that liver allografts are not only being well accepted, but, moreover, can facilitate the acceptance of skin grafts from the liver donor; whereas third party skin grafts, in contrast, are rapidly rejected (23). Oral tolerance, which is induced by oral administration of antigen, seems to be at least in part facilitated by the liver (24). Furthermore, the inventors have previously shown that hepatic tolerance could be utilized to induce neuroantigen-specific Treg and protection from autoimmune neuroinflammatory disease (25), using gene transfer to liver cells. The generation of Treg cells was thymus-independent, required ectopic expression of neuroantigen in the liver, and occurred by conversion from conventional $CD4^+CD25^-$ T cells (25, 34). It was suggested that gene delivery to hepatocytes might be useful for therapy of human autoimmune disease (25, 33).

In light of the state of the art, the inventors solved the problem of providing a pharmaceutical composition capable of inducing regulatory T cells, and thus useful for treating and preventing a disease wherein suppression of a specific immune response is beneficial, e.g. an autoimmune, disease, an allergy or a disease wherein inflammation is excessive, chronic or adverse, wherein said pharmaceutical composition is suitable for use in human subjects and avoids, e.g., problems potentially associated with gene transfer.

The present invention provides a pharmaceutical composition comprising a nanoparticle, said nanoparticle comprising
a) a micelle comprising an amphiphilic polymer rendering the nanoparticle water-soluble, and
b) a peptide comprising at least one T cell epitope associated with the outside of the micelle, for use in generating regulatory T cells specific to said at least one T cell epitope in a subject.

In the context of the invention, the term "nanoparticle" is used interchangeably with "nanoscale particle". Such particles have a diameter of 1-999 nm, preferably, of about 2 to about 600 nm, about 5 to about 500 nm, about 10 to about 300 nm, about 30 to about 100 nm, about 40 to about 50 nm.

The inventors have found that, after in vivo administration to a subject of the specific nanoparticles of the invention associated with a peptide, these nanoparticles locate in the liver, in particular, in liver sinusoidal endothelial cells, and they are capable of inducing regulatory T cells specific to the associated peptide. The induced regulatory T cells were capable of suppressing experimental autoimmune encephalitis (EAE) in an animal model.

Previously, nanoparticles had been found to localise in a variety of tissues, including liver cells (35-38), and they had also been found to have a diverse variety of effects on the immune system (36-38). Both the predominant localisation of the presently administered nanoparticles in liver sinusoidal endothelial cells and the clear induction of regulatory T cells by the nanoparticles of the invention was therefore surprising.

The nanoparticles used in the invention comprise a micelle comprising an amphiphilic polymer rendering the nanoparticle water-soluble. In the context of the present invention, the term "micelle" relates to an aggregate of amphiphilic molecules dispersed in an aqueous solution. The hydrophilic parts of the amphiphilic molecules are in contact with the surrounding solvent, sequestering the hydrophobic "tail" regions of the amphiphilic molecules on the inside of the micelle, and thus render the nanoparticle water-soluble. This type of micelle is also known as a normal phase micelle (or oil-in-water micelle). In the context of the invention, the micelle is formed by a single layer of an amphiphilic polymer. It is clear for the skilled person that such a micelle is structurally distinct from a bilayer or a liposome formed by an amphiphilic polymer. Such structures are not, or not to a significant percentage (e.g. not more than 10%, more than 5%, or preferably, more than 1%), comprised in the pharmaceutical composition.

In a preferred embodiment, the amphiphilic polymer forming the micelle is a synthetic polymer. It may comprise a hydrophobic region comprising a hydrophobic, e.g., carboxylic, "tail" having a length of about 14-22, preferably, 16-18 C atoms. The hydrophilic region of the polymer may be negatively charged in an aqueous solution. The molecular mass of the polymer may be, e.g., about 30 000-50 000 g/mol. Preferably, the polymer is a maleic copolymer, such as poly(maleic anhydride-alt-1-octadecene) (available, e.g., from Sigma Aldrich). The polymer may also be, e.g., poly (maleic anhydride-alt-1-tetradecene) or polyisoprene-block polyethyleneoxide block copolymer (PI-b-PEO). The micelle may be formed by one, but also by more than one, e.g., two, three or four amphiphilic molecules, in particular, polymers. In general, in the context of the specification, "a" or "the" is not intended to be limiting to "one" unless specifically disclosed.

Figure 3A:
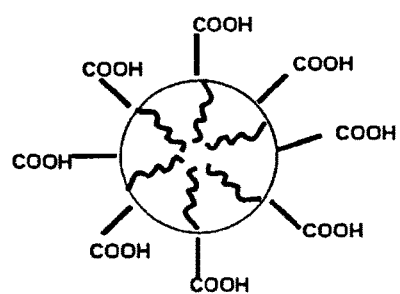

In one embodiment of the invention, the core of the micelle does not comprise additional molecules or compounds, but consists of the hydrophobic regions of the amphiphilic polymers (such a micelle is schematically shown in FIG. 3A).

In another embodiment, the micelle coats a solid hydrophobic core (as schematically shown in FIG. 3B), which preferably is an inorganic core. The inorganic core preferably is a traceable inorganic core, e.g., comprising iron oxide, CdSe, silver or gold. The diameter of the core is about 2 to about 500 nm, preferably, about 5 to about 30 nm, more preferably, about 9 to about 12 nm.

Exemplary inorganic cores are FeO nanoparticles stabilized by oleic acid or another carboxylic acid (C14-C22, preferably, C16-18), quantum dots (CdSe/CdS/ZnS stabilized, e.g., by trioctyloxinphosphinoxide), gold nanoparticles, e.g., stabilized by sulfonic compounds. Such inorganic cores by themselves are typically not stable in an aqueous solvent such as water, but embedding them in the polymeric micelles renders them water-soluble. The hydrophobic parts of the amphiphilic polymer interact with the hydrophobic core of the nanoparticle, leading to formation of a single coating layer of polymer surrounding the core.

The cores preferably render the nanoparticles of the invention traceable, e.g., by their characteristics in fluorescence, electron microscopy or other detection method.

In a preferred embodiment of the invention, the nanoparticle comprises an iron oxide core having a diameter of about 9 to about 12 nm encapsulated by a coating of poly(maleic anhydride-alt-1-octadecene) to which a peptide comprising a T cell epitope is linked, preferably, covalently linked. According to one embodiment, the nanoparticles comprise a lipophilic iron oxide core, synthesized according to a method of Colvin (26), preferably, with a modification of the reaction time to produce particles of about 9-12 nm as described in the examples. According to one embodiment, iron oxide nanoparticles are encapsulated by incubation with poly(maleic anhydride-alt-1-octadecene) solution according to a protocol modified from (27) to produce water-soluble particles.

The nanoparticle, by virtue of the polymer forming the micelle, may be negatively charged or uncharged, preferably, it is negatively charged. The polymer coating may comprise acid, e.g., carboxylic acid, groups, leading to a negative charge.

The peptide is preferably covalently linked to the micelles, e.g., by carbodiimide or succinimide coupling, e.g., conjugation via 1-Ethyl-3-(3-dimethylaminopropyl) carbodiimide, (as, e.g., in the example 4 below), or by another method of covalently coupling peptides. The peptide is localized on the outside of the micelles. The peptide may also be non-covalently associated to the nanoparticle. Such nanoparticles may be prepared, e.g., by dipping and drying as described by Giri et al. (36).

The term "peptide" is not intended to be limiting in size, in particular, the peptide may comprise a whole protein or about 8 to about 2000 amino acids, preferably, 8-200 amino acids, 8-100 amino acids, 9-60 amino acids, or 10-20 amino acids. The term also comprises combinations of different peptides, which may be linked to each other as fusion polypeptides. The peptide comprises at least one T cell epitope to which regulatory T cells are to be generated. At least one epitope needs to be capable of being presented by cells of the subject to which the nanoparticles are to be administrated, i.e., the peptide and/or the subject need to be appropriately selected. Preferably, the peptide comprises several epitopes which enable it to be presented in a plurality of Major Histocompatibility Complex types.

As the regulatory T cells are predominantly CD4+, presentation on MHC class II is of main interest in this respect. The phenotype of a subject, e.g., a human subject, can easily be tested. Epitopes of a specific peptide which can be presented on specific MHC molecules are known and/or can routinely be selected, e.g., by appropriate software. Preferably, the peptide comprises a sufficient number and selection of epitopes to enable it to be presented by at least 20%, preferably, at least 30%, at least 40%, at least 50%, at least 60%, at least 70%, at least 80% or at least 90% of a population of subjects, wherein, the population of subjects may be the general population, or, preferably, a population of subjects having a certain disease, condition or disorder associated with the peptide as described below. Preferably, the subject is human, but it can also be mouse, rat, rabbit, guinea pig, pig, ape, monkey, cattle, sheep, goat, cat or dog.

The peptide may be synthesized, recombinantly expressed or isolated or modified from natural sources. The peptide, or at least the epitope against which regulatory T cells are to be generated, is preferably derived from a peptide/protein against which an inflammatory immune response is to be suppressed, e.g., in the context of treatment or prevention of an autoimmune disease or an allergy. The peptide may, e.g., be an allergen, a known autoimmune antigen, or a fragment or derivative thereof. The peptide can combine various epitopes from various antigens.

The inventors have found that nanoparticles of the present invention are suitable for transferring the peptide to liver sinusoidal endothelial cells of a subject in vivo. As described below, other cells are also targeted, however—without intending to be bound by the theory—targeting to liver sinusoidal endothelial cells seems to be important for the generation of regulatory T cells, as the pharmaceutical composition induces generation of regulatory T cells specific for the at least one epitope via presentation of said epitope by liver sinusoidal endothelial cells. Preferably, at least 60% of the nanoparticles found in the liver after administration localize in liver sinusoidal endothelial cells, more preferably, at least 70% or at least 80%. A smaller percentage may also be found in Kupffer cells or in endothelial cells of intestinal veins that feed the portal vein.

The nanoparticles used in the present invention may be selected by their ability to be loaded with cargo peptide and by their ability to target such cargo peptide to liver cells, notably liver sinusoidal endothelial cells.

The nanoparticles may comprise a moiety, e.g., a carbohydrate or a protein targeting them, or enhancing targeting to specific cells such as liver sinusoidal endothelial cells and/or Kupffer cells. Such moiety could, e.g., enhance or accelerate uptake from the circulation via receptor mediated endocytosis. Examples of suitable modifications are carbohydrates such as mannose. However, the inventors have shown that, advantageously, such additional targeting moieties are not required in the context of the invention.

The pharmaceutical composition of the invention may further comprise at least one suitable excipient and/or diluent. The diluent preferably is water or water-based, e.g., a buffer such as Phosphate buffered saline (PBS), Ringer solution or sodium chloride solution. Suitable preservatives may or may not be contained. It is evident that, in particular for administration to a human subject, the composition preferably is sterile and biologically compatible.

The pharmaceutical composition may further comprise a cytokine such as TGFβ.

The nanoparticles are preferably used in and formulated for administration to a subject having a disease wherein suppression of a specific immune response is beneficial.

The required dose and concentration for administration to the subject may be determined by the responsible medical attendant according to the facts and circumstances of the case. An exemplary dose might comprise 0.1 to 10 mg/kg body weight, preferably, about 0.5-2 mg/kg body weight or about 1 mg/kg body weight, e.g., for a human subject. Administration may be repeated, e.g., twice, three or four times, e.g., with, 1, 2, 3, 4, 5, 6, 7, 10 or 14 days between administrations.

Preferably, the pharmaceutical composition is for use in treating or preventing a disease wherein suppression of a specific immune response is beneficial, wherein said disease is selected from the group comprising an autoimmune disease, an allergy or a disease wherein inflammation is excessive, chronic or adverse. Such a disease may be associated with excessive or chronic inflammation. The nanoparticles may also be for use in treating clinical conditions associated with an adverse outcome of inflammation. Diseases and inflammatory conditions that may be treated by the pharmaceutical composition of the invention include, but are not limited to, multiple sclerosis, type I diabetes, rheumatoid arthritis, systemic lupus erythematosus, degeneration after trauma or stroke, graft versus host disease, transplant rejection, inflammatory bowel disease (IBD), asthma, allergies, e.g., allergic rhinitis, allergic eczema and the like;

The term 'treating' as used herein refers to the alleviation of symptoms of a particular disease, in a subject, and/or improvement of an ascertainable measurement associated with a particular disorder.

The invention further provides a method comprising administering to a subject in need thereof a pharmaceutical composition comprising a nanoparticle as defined herein. As described, such nanoparticles may be loaded with autoantigen, alloantigen or other antigen to which the adverse inflammatory response is directed, or with peptides comprising an amino acid sequence derived or modified from such antigen.

The invention further provides a method of generating regulatory T cells, comprising,
after administration of a nanoparticle as defined herein to a subject;
and after taking a sample comprising T cells from said subject;
isolating regulatory T cells from said sample.

A sample comprising T cells may, e.g., be a biopsy, a blood sample, a sample from spleen, liver or any organ targeted by an allergy or autoimmune disease which is associated with the peptide employed in the method. The isolation step may be based on selection of regulatory T cell markers such as CD4, CD25, CD127 and/or FoxP3. For example, sorting by flow cytometry or adhesion to antibody coated beads, e.g.; magnetic beads, may be used. Isolated cells may be used for analytic purposes, e.g., for determining if regulatory T cells have been induced, or for determining their characteristics. If further culture of cells is of interest, intracellular staining of FoxP3 is not employed for selection.

After isolation of the regulatory T cells, they may be further cultured and or expanded, e.g., in the presence of the T cell epitope and/or a cytokine such as TGFβ, IL-2, IL-35, IL-10. Regulatory T cells generated in this matter may be useful for scientific purposes. They may also be for use in treating a subject in need thereof, e.g., a subject having a disease or condition as described above, e.g., after expansion. Regulatory T cells obtainable by the method may be formulated as a pharmaceutical composition to this end. The invention is thus also directed to a method of preparing a pharmaceutical composition comprising the method of generating regulatory T cells.

While it has for some time often been possible to generate protective, e.g., inflammatory, immune responses in subjects e.g., humans, to protect them, e.g., against diseases elicited by pathogens, a method to inhibit efficiently and specifically adverse immune reactions in humans, e.g., in the context of autoimmune diseases, chronic inflammations and allergy has long been looked for. The present invention at last provides pharmaceutical compositions and methods for generating specific regulatory immune cells, which are, as demonstrated in a model system, even capable of suppressing autoimmune disease.

All literature cited herein is herewith fully incorporated by reference. The examples provided below are intended to illustrate exemplary embodiments of the invention without limiting its scope.

FIGURE LEGENDS

FIG. 1: Efficient generation of Treg cells from CD4+ CD25− non-regulatory T cells by various liver cell types, but not by splenic dendritic cells.

Figure 2:
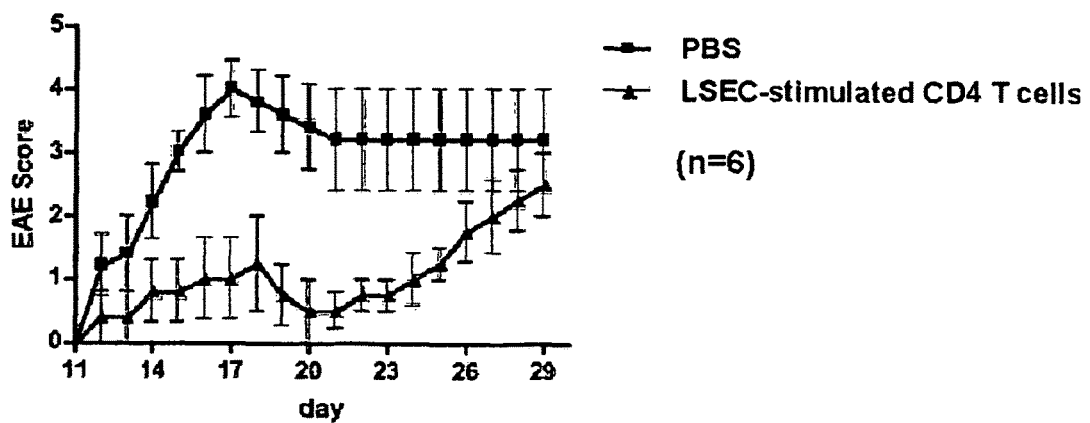

FIG. 2: Amelioration and delayed onset of experimental autoimmune neuroinflammation by transfer of LSEC-stimulated neuroantigen-specific T cells.

FIG. 3: Schematic design of exemplary micelles for targeted delivery of peptides to liver cells. A: A micelle formed by an amphiphilic polymer. The hydrophobic parts of the polymer form the center of the micelle, while the hydrophilic parts are turned to the outside and render the micelle water-soluble. In the example shown, the hydrophilic parts are negatively charged. B: A micelle, formed as in A, coats a solid core. The solid core may be, e.g., an inorganic core such as an FeO nanoparticle stabilized by oleic acid molecules. The hydrophobic parts of the polymer interact with the hydrophobic core, thus forming a micelle around the core.

FIG. 4A: Fluorescent nanoparticles of the invention are rapidly and specifically taken up from the circulation and accumulate predominantly in liver sinusoidal endothelial cells (LSEC), as demonstrated by intravital microscopy. In addition to the fluorescent nanoparticles taken up in the LSEC lining the hepatic sinusoids, nuclei (round) are stained with DAPI.

Figure 4B:
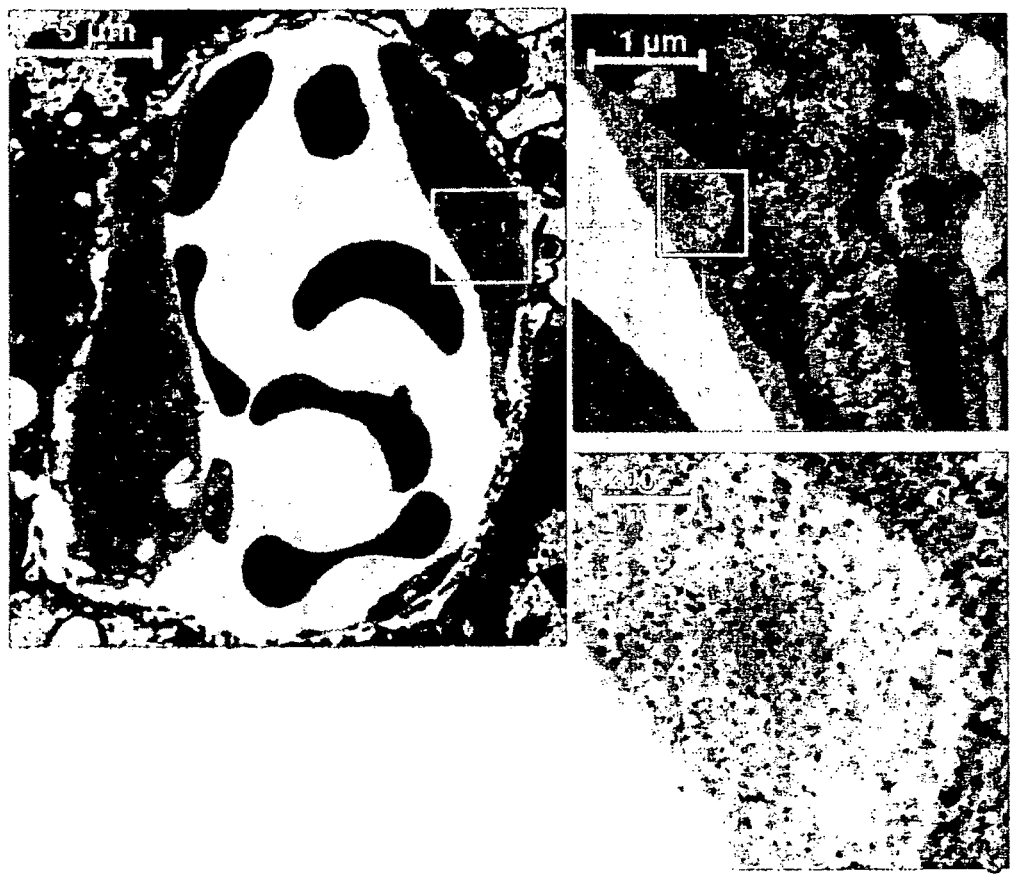

FIG. 4B: Confirmation of localization of nanoparticles of the invention in liver sinusoidal endothelial cells by transmission electron microscopy.

Figure 4C:
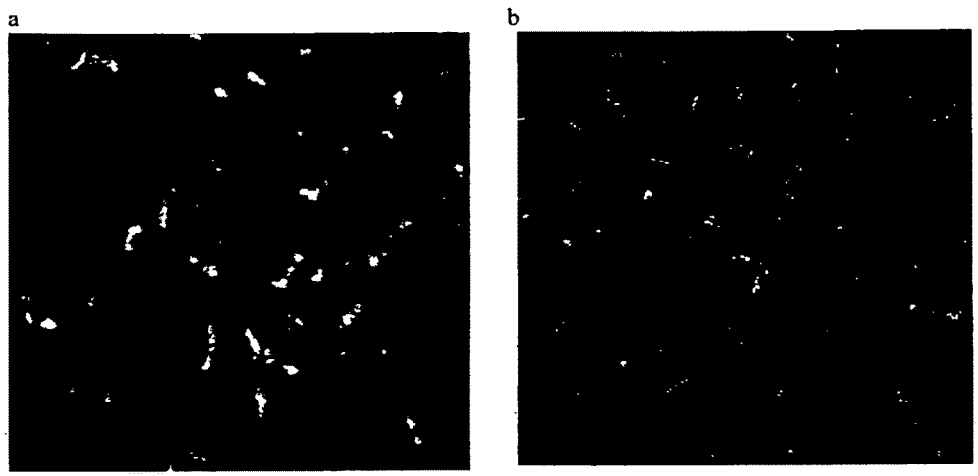

FIG. 4C: Nanoparticles embedded in recombinant triglyceride rich lipoprotein liposomes prepared according to Bruns et al., 2009, are specifically taken up from the circulation and accumulate predominantly in Kupffer cells, as demonstrated by intravital microscopy (a) in control treated mice. (b) In clodronate-treated mice, wherein Kupffer cells were depleted, uptake of the liposomal nanoparticles is significantly reduced, confirming accumulation in Kupffer cells in normal mice.

Figure 5:
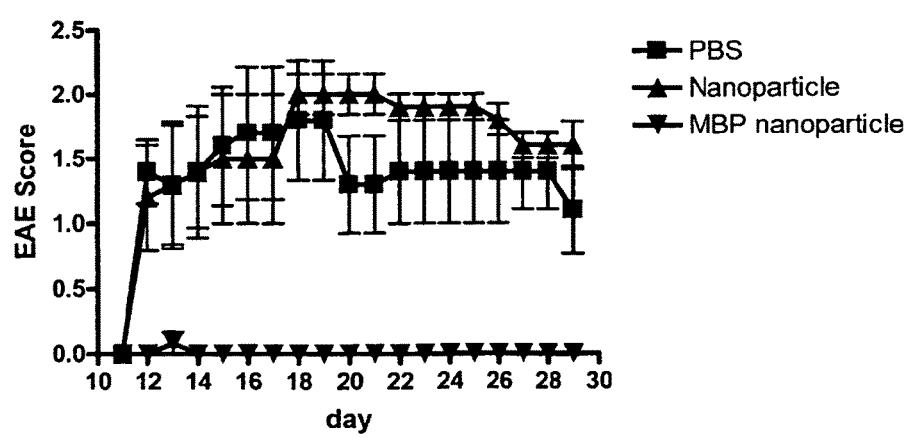

FIG. 5: Targeted delivery of neuroantigen peptide to liver cells by peptide-nanoparticle conjugates, but not peptide-free nanoparticles induces full protection from clinical neuroinflammatory disease.

Figure 6:
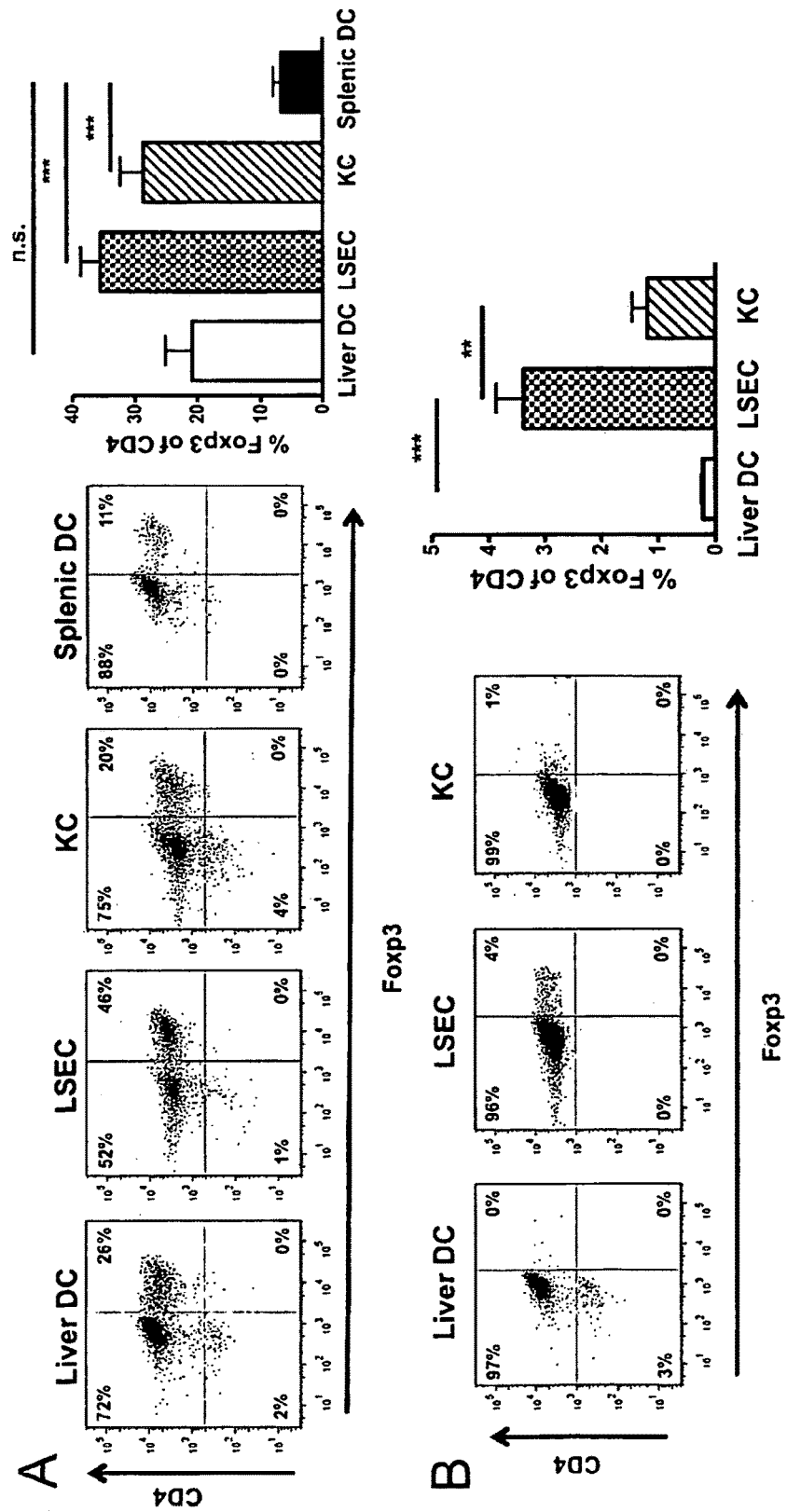
Figure 6:
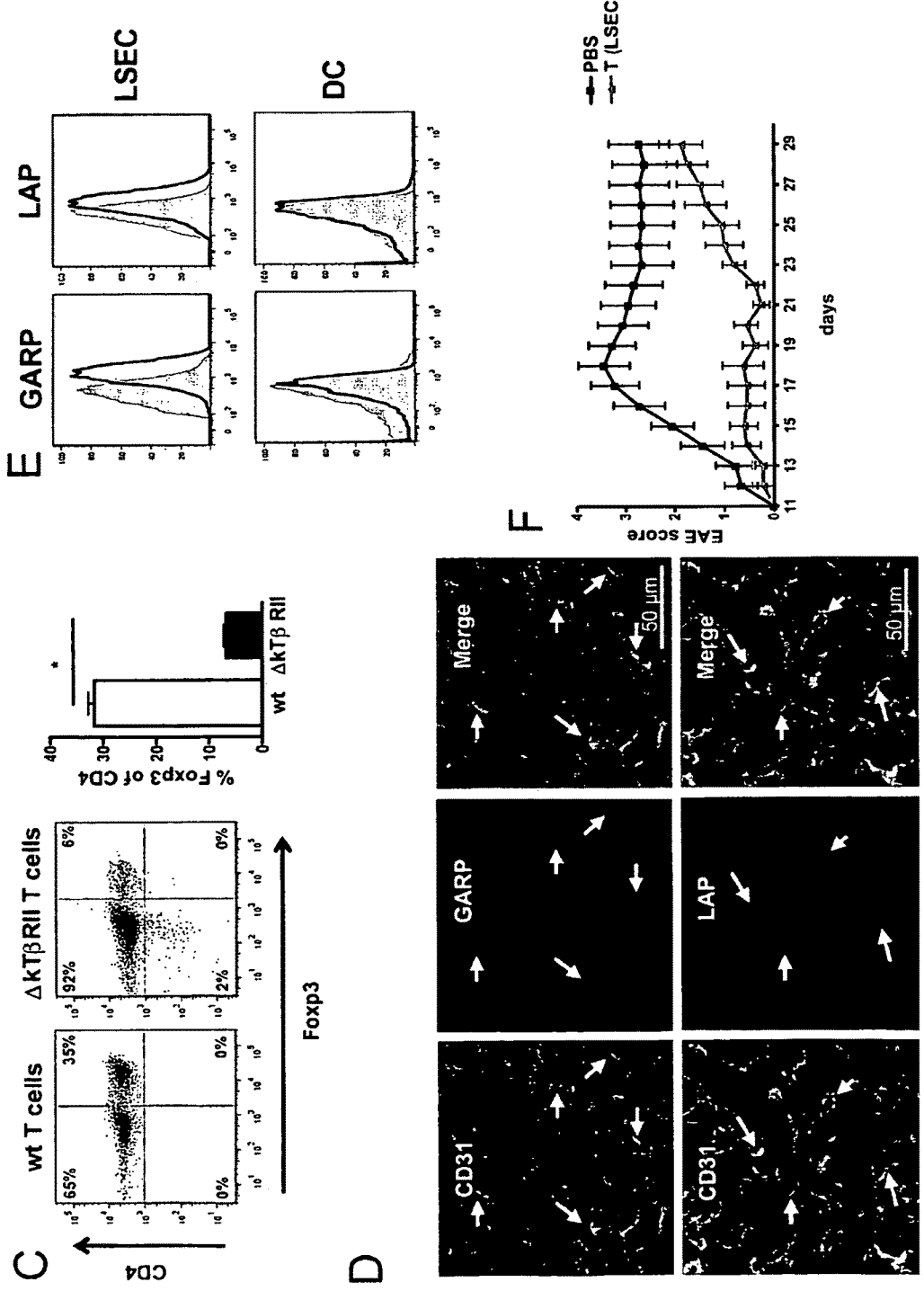

FIG. 6: TGFβ dependent Treg conversion by liver antigen-presenting cells. MBP-specific CD4+Foxp3− non-Tregs were stimulated with MBP peptide by liver DC, LSEC, KC or splenic DC in presence (A) or absence (B) of TGFβ and conversion rates to Foxp3+ Tregs were determined. C) Defective Treg conversion by TGFβ-insensitive CD4 T cells. D) Colocalization of GARP or LAP and CD31 on liver sections of wild-type mice revealed by confocal microscopy. E) Expression of GARP and LAP (solid lines) by freshly isolated LSEC (upper panels) or splenic DC (lower panels) determined by flow cytometry (isotype controls in grey). F) MBP-specific CD4+CD25− non-Tregs were stimulated by LSEC with MBP peptide and transferred to B10 μL mice (10 5 cells/mouse; n=8), in which EAE had been induced. Control mice received PBS (n=9). Mean EAE scores±s.e.m. are shown; P=0.0025.

Figure 7:
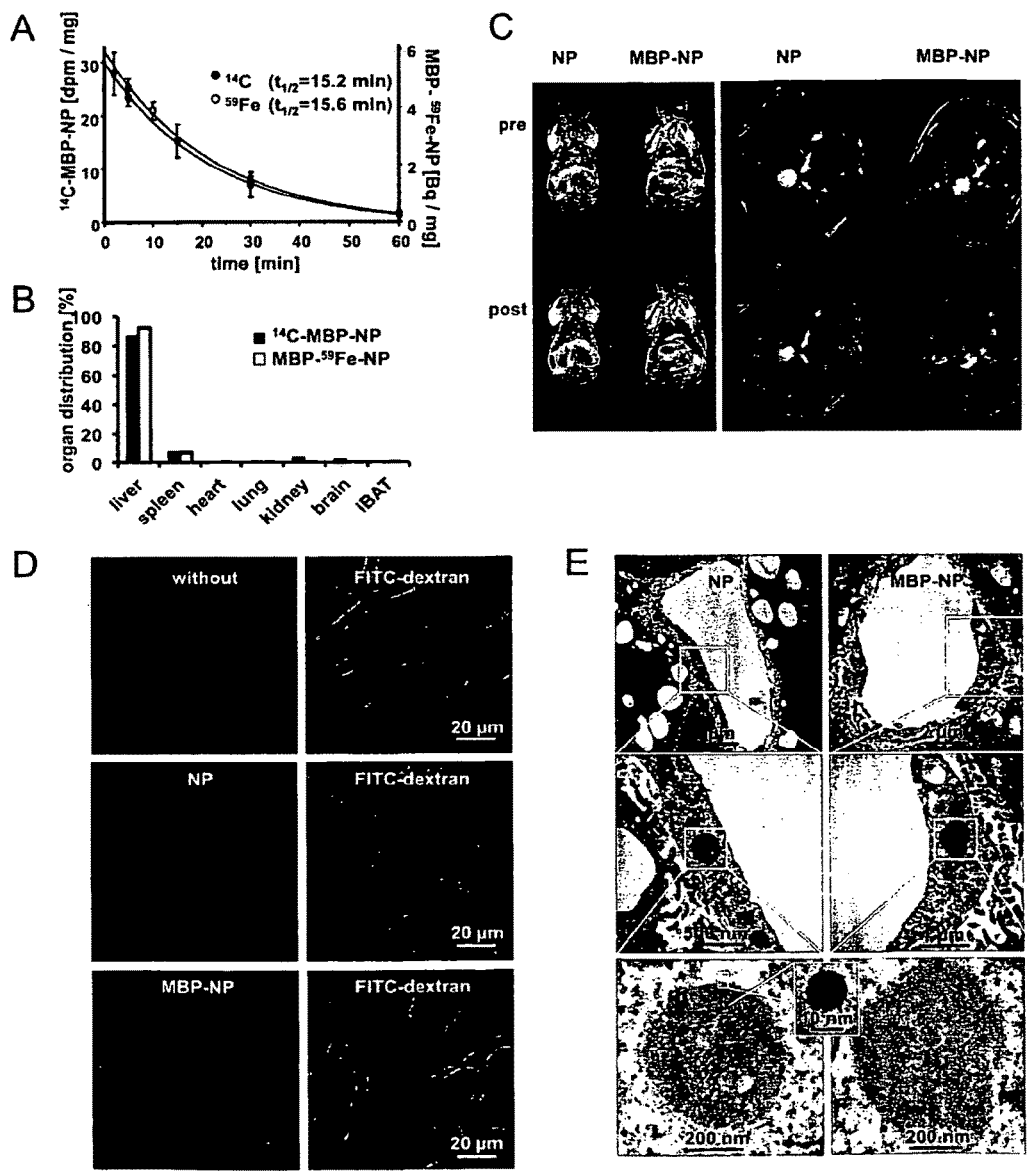

FIG. 7: Targeted delivery of MBP peptides to LSEC with nanoparticles. A) Plasma clearance rates of MBP peptide coupled to $^{59}$Fe—NP (MBP—$^{59}$Fe—NP) and $^{14}$C-MBP peptide coupled to unlabeled NP ($^{14}$C-MBP-NP). B) Organ distribution of MBP—$^{59}$Fe—NP and $^{14}$C-MBP—NP 60 min after intravenous injection. Mean values±s.e.m. are shown (n=4). C) Representative coronal and transversal MR images of mice pre and post injection of unloaded NP or MBP—NP. D) Intravital confocal microscopy of the liver showing uptake of MBP—NP or unloaded NP by LSEC. Nuclei were also stained. right panel: LSEC (FITC-dextran), left panel: quantum dot-labeled NP; scale bar: 20 μm. E) Electron microscopy of liver, 60 min after intravenous injection of MBP—NP or unloaded NP.

Figure 8:
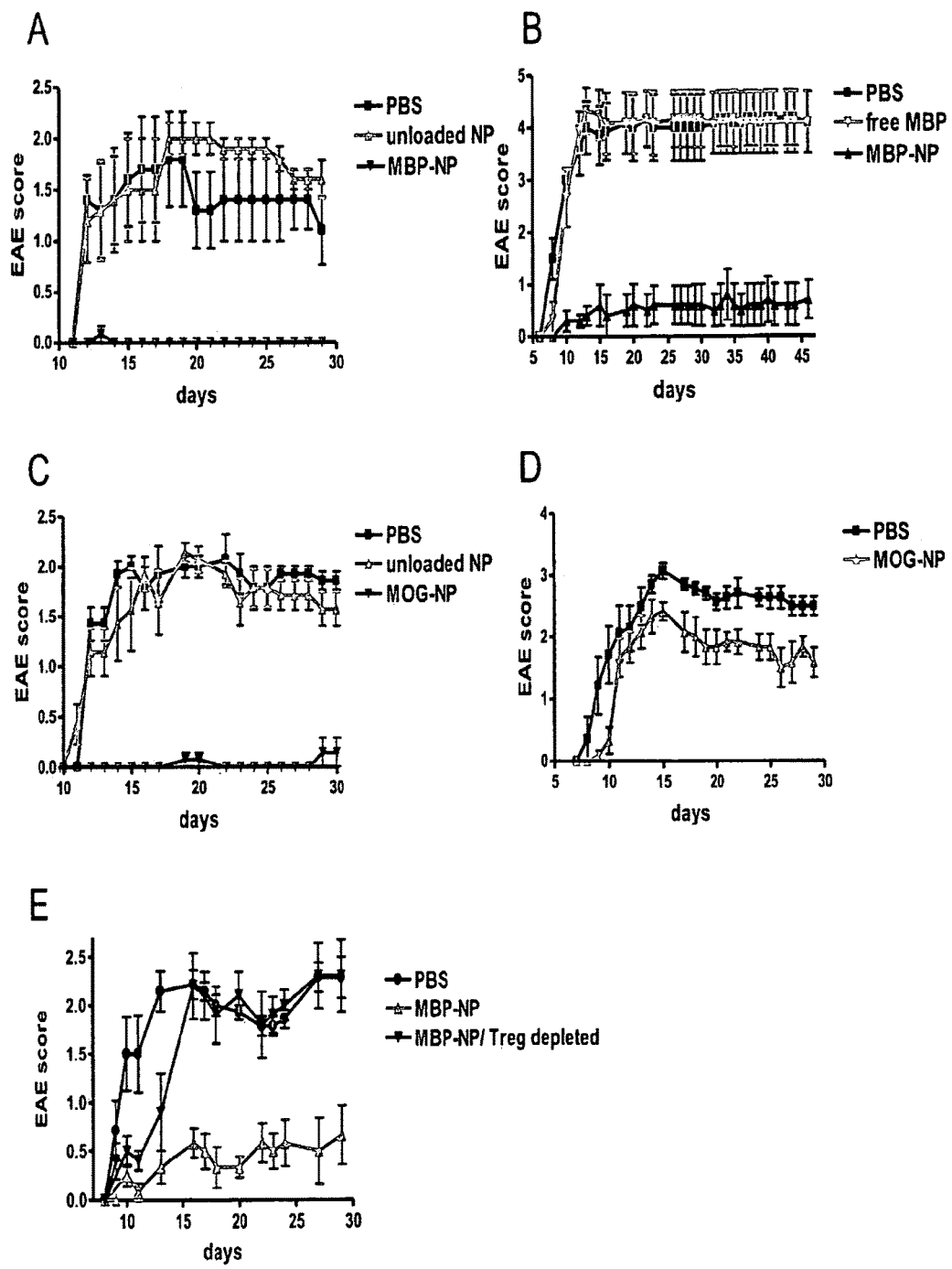

FIG. 8: Nanoparticle-based delivery of neuroantigen peptides to LSEC prevents EAE induction. EAE was induced in B10 μL wildtype mice (A, E) or tg4 mice (B) by immunization to MBP. In C57BL/6 wildtype mice (C) or hCD2-ΔkTβRII mice (D), EAE was induced by immunization to MOG. One day after EAE induction, mice were injected once intravenously with PBS (A-E) or neuroantigen peptide-loaded nanoparticles (MBP—NP (A, B, E) or MOG-NP (C, D,). As control, mice received equivalent amounts of unloaded NP (A, C) or unconjugated MBP peptide (⁻B,). E, Twice per week, mice treated with MBP—NP were intraperitoneally injected with Treg-depleting PC61 antibody (MBP—NP/Treg-depleted) or isotype-matched control antibody (MBP—NP). Shown are mean EAE scores±s.e.m. (n=5-7).

Figure 9:
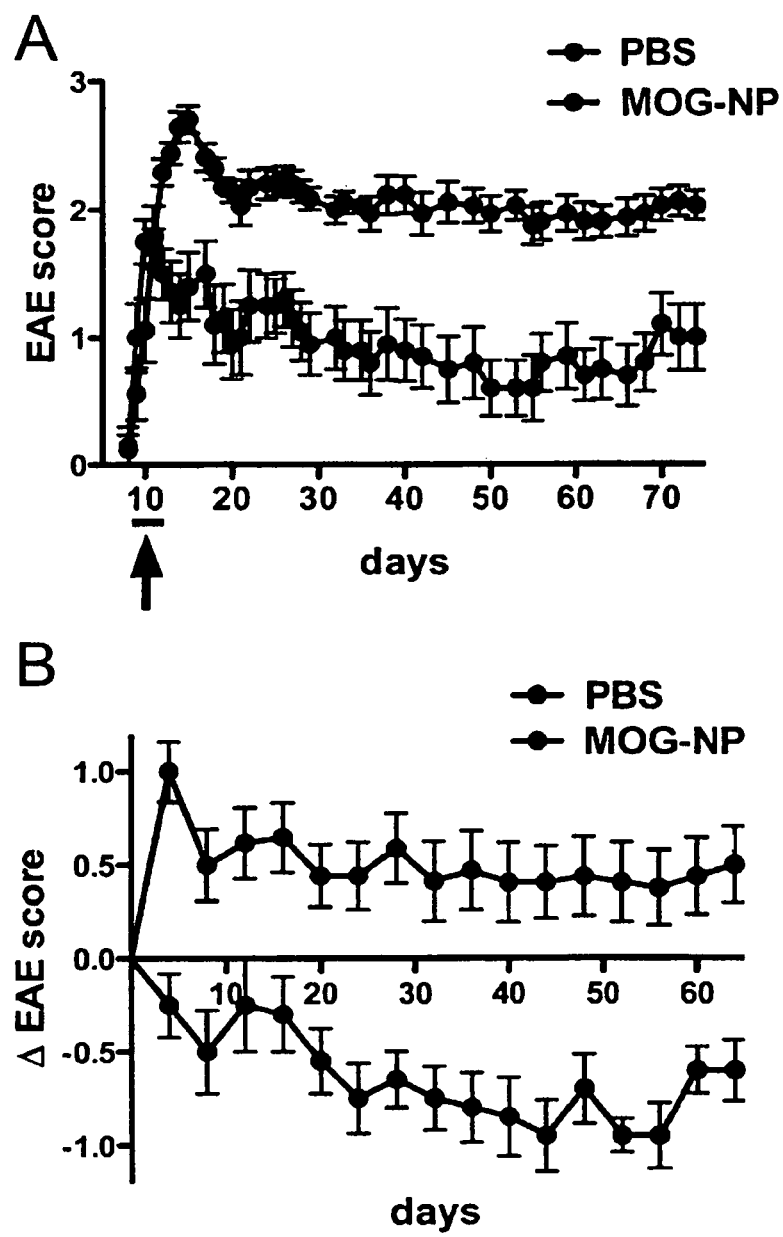

FIG. 9: Therapy of established EAE by nanoparticle-based transfer of MOG peptide to LSEC. EAE was induced in C57BL/6 mice by immunization to MOG. After disease onset (day 8-12, indicated by arrow), mice were treated with a single injection of MOG-loaded nanoparticles (n=10, grey line) or PBS (n=17, black line). A) EAE course over an extended observation period of more than nine weeks after MOG-NP (grey) or PBS (black) treatment, Shown are mean EAE scores±s.e.m. B) Change of mean individual disease score after treatment with MOG-NP (gray) or PBS (black); "EAE score=score difference compared to the time of treatment.

Figure 10:
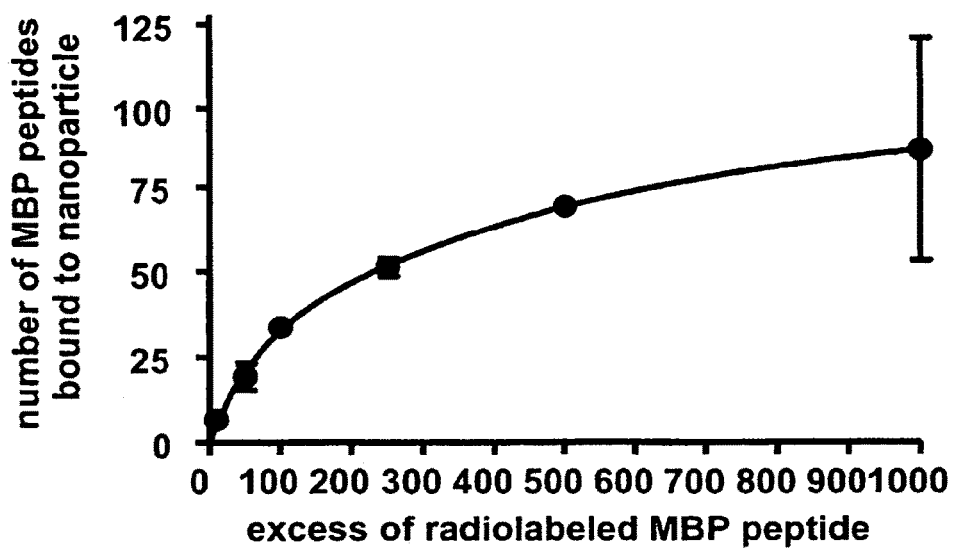

FIG. 10: Coupling efficiency of peptide to NP. Calculated number of peptide molecules coupled to NP after incubation with increasing amounts of radiolabeled MBP peptide. Mean values±s.e.m. are shown (n=3).

Figure 11:
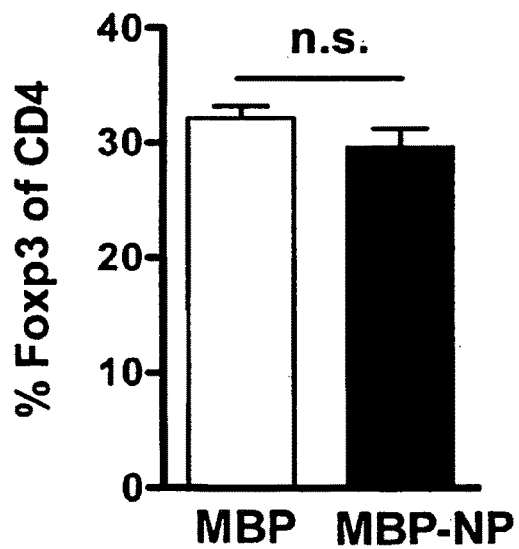

FIG. 11: Efficient Treg conversion by LSEC in vitro using nanoparticle-conjugated MBP peptide or free MU peptide. Splenic CD4+Foxp3− T cells from tg4×Foxp3gfp.KI mice were co-cultured with LSEC in the presence of TGFβ (2 ng/ml) and free MBP peptide (5 ng/ml) or an equivalent dose of MBP peptide coupled to nanoparticles (MBP—NP) for four days. Foxp3 induction in CD4 T cells was then analyzed by flow cytometry. For statistical analysis, Mann-Whitney test was performed (free MBP: 32.16±1.075; MBP—NP: 29:63±1.558; P=0.2857). n.s.=not significant.

Figure 12:
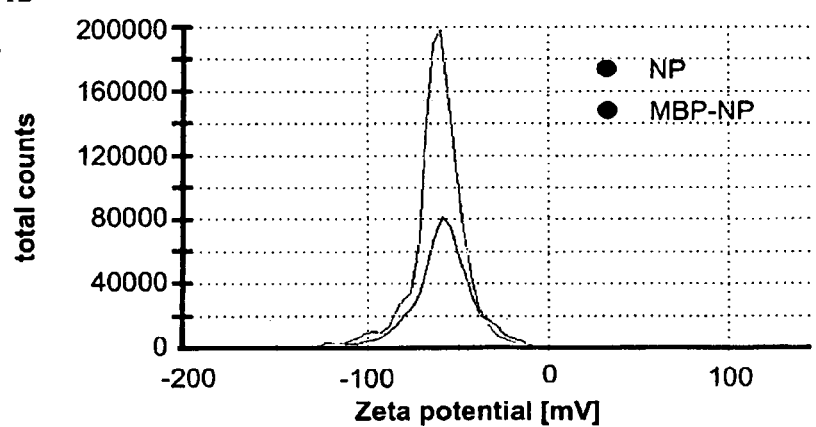
Figure 12:
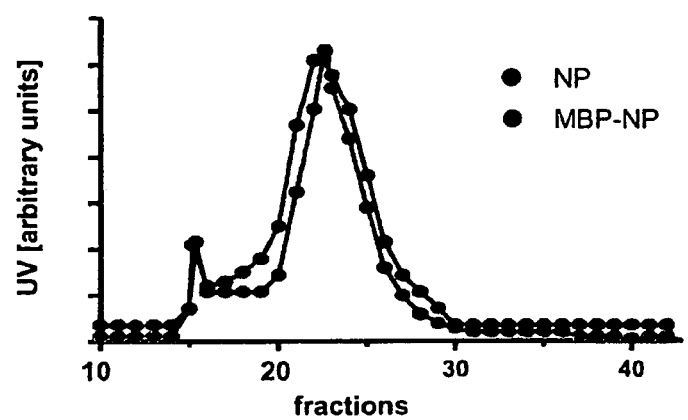
Figure 12:
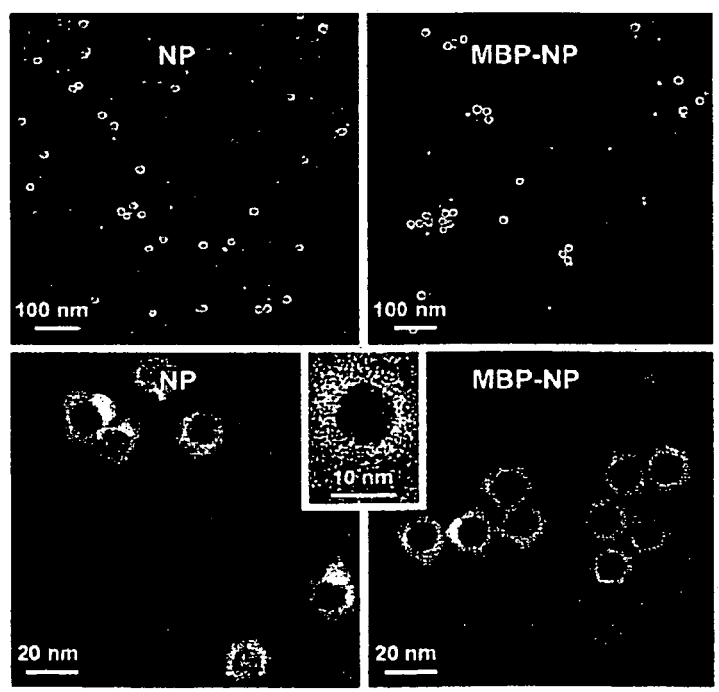

FIG. 12: Characteristics of NP and MBP—NP. A) The Zeta potentials of NP and MBP—NP were measured at 20° C. using a Malvern Zetasizer Nano-ZS instrument. Both samples exhibit a comparable negative surface charge (averaged Zeta-potential of NP −58 mV; MBP—NP −61.6 mV) (MBP—NP: higher peak; NP: lower peak). No differences in size could be detected by B) size exclusion chromatography (MBP—NP: left line; NP: right line) or C) by transmission electron microscopy. For electron microscopy, samples were stained with 1% sodium silicotungstate, pH 7, so that the organic shell appears light and the iron oxide core dark.

Figure 13:
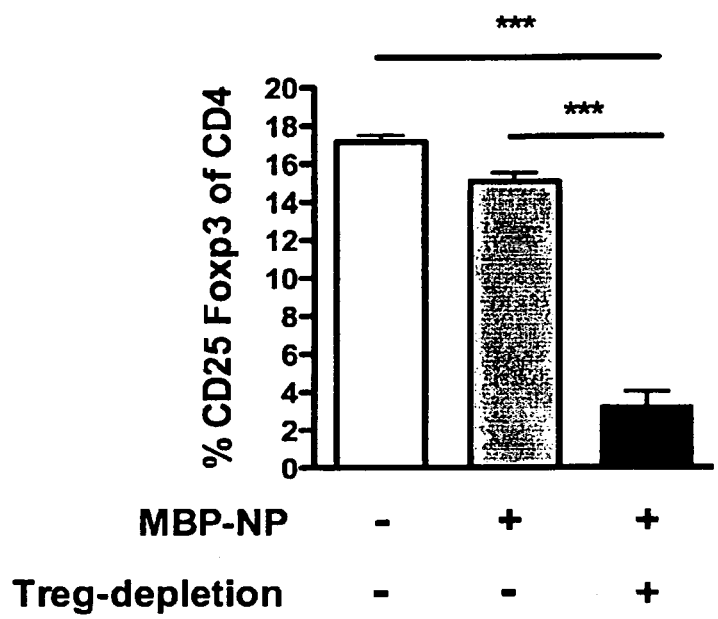

FIG. 13: Depletion of CD25+Foxp3+CD4+ Treg in vivo by repeated PC61 antibody-administration. B10 μL mice were immunized to MBP peptide and treated on the next day with PBS (n=7) or MBP peptide-coupled nanoparticles (MBP—NP). Mice, which received MBP—NP, were then either treated twice per week with Treg-depleting PC61 antibody (n=5) or non-depleting isotype-matched control antibody (n=6). Mice were sacrificed on day 29 post immunization and spleens were analyzed for Treg depletion efficiency by flow cytometry. Results are depicted as mean % of CD25+Foxp3+ of CD4+ T cells±s.e.m. (PBS 17.16±0.3422; MBP—NP+isotype 15.08±0.8594; MBP—NP+PC61 3.160±0.4643; P<0.001). For comparison of multiple groups, one-way ANOVA and Tukey's post test were performed.

Figure 14:
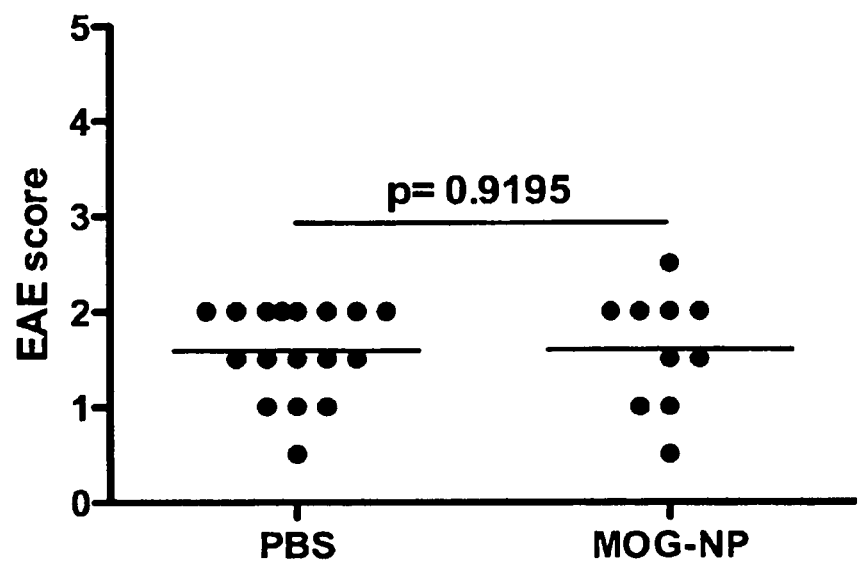

FIG. 14: Initial EAE scores at the time of therapeutic MOG-NP or PBS administration. C57BL/6 mice were immunized to MOG peptide and developed clinical EAE symptoms. After disease onset (day 8-12), mice were treated with a single injection of MOG-loaded nanoparticles (n=10) or PBS (n=17); at the time of treatment, the mean initial disease scores between groups were indifferent (mean±s.e.m.: 1.59±0.12 vs. 1.60±0.19; P=0.9195).

EXAMPLES

Example 1: Generation of Regulatory T Cells by Liver Sinusoidal Endothelial Cells and Kupffer Cells Mouse liver non-parenchymal cells were isolated applying a protocol modified from (28). Briefly, mouse livers were perfused with 0.05% collagenase IV (Sigma; Taufkirchen, Germany) in Gey's balanced salt solution, mechanically dissected and further digested in 0.05% collagenase IV in Gey's balanced salt solution for 25 minutes at 37° C. at constant rotation (240 rpm). Hepatocytes and debris were sedimented twice at 40 g and non-parenchymal cells were recovered by centrifugation over a 17% Optiprep (Sigma) gradient at 400 g.

Liver sinusoidal endothelial cells (LSEC) were purified from the non-parenchymal cells as described (29) by magnetic sorting with the ME-9F1 antibody (Miltenyi Biotech, Bergisch-Gladbach, Germany). LSEC were seeded on collagen-coated culture plates (Serva, Heidelberg, Germany). After overnight culture in Iscove's modified Dulbecco's medium supplemented with 5% FCS, non-adherent cells were removed by medium change. Accordingly, Kupffer cells were purified from the non-parenchymal cells by magnetic sorting with biotinylated F4/80 antibody (eBioscience, Frankfurt, Germany) and anti-biotin microbeads (Miltenyi).

Alternatively, hepatocytes were isolated from mouse livers as described (30); and dendritic cells were isolated from mouse spleen by magnetic cell separation for CD11c as described (30).

$10^5$ LSEC, $10^5$ Kupffer cells, or $5\times10^3$ hepatocytes were seeded into 96-well plates, and used on the following day for stimulation of CD4+CD25− T cells. Alternatively, $5\times10^4$ dendritic cells, were seeded into 96-well plates, and used on the same day for stimulation of CD4+CD25− T cells. These CD4+CD25− non-regulatory T cells were isolated from mouse spleens by magnetic cell separation, and $5\times10^5$ purified lymphocytes per well were then stimulated on the indicated antigen presenting cells in serum-free medium (Pan Biotech, Aidenbach, Germany) with solute antibody to CD3 (BD Bioscience, Heidelberg, Germany). After four days of culture, the T cells were harvested and analysed by flow cytometry for the percentage of CD4+CD25+FOXP3+ Treg cells. As indicated, transforming growth factor-beta (TGFβ) was added to some stimulation cultures.

Results: As shown in FIG. 1, dendritic cells were poor inducers of Treg. In the absence of exogenous TGFβ, the generation of Treg cells induced by dendritic cells was negligible, and in the presence of exogenous TGFβ, only 7.5% of the dendritic cell-stimulated T cells were Treg. In contrast, the various liver cell types—LSEC, Kupffer cells and hepatocytes—were efficient inducers of Treg, at least in the presence of exogenous TGFβ, with at least 20% of the liver cell-stimulated T cells being Treg. Notably LSEC were efficient Treg generators, since, in the presence of TGFβ, 38% of the stimulated cells were Treg, and, even in the absence of exogenous TGFβ, 16.3% of the stimulated T cells were Treg.

Example 2: Suppression of Experimental Autoimmune Neuroinflammation by Liver Sinusoidal Endothelial Cell-Stimulated CD4 T Cells LSEC were isolated as described in example 1 and used to stimulate non-regulatory CD4+CD25− T cells purified from tg4 mice, which carry a transgenic T cell receptor specific for myelin-basic protein (25). After 4 days of T cell stimulation with the specific myelin basic protein-peptide (5 ng/ml) on LSEC, performed as described in example 1, $10^5$ LSEC-stimulated T cells were transferred to B10 μL mice that had been immunized one day before with a myelin basic protein peptide to induce the clinical symptoms of experimental autoimmune encephalomyelitis (EAE), as described in (25).

Results: Adoptive transfer of LSEC-stimulated myelin basic protein-specific T cells induces a delayed and strongly ameliorated course of EAE, indicating that LSEC-induced neuroantigen-specific Treg cells are capable of improving autoimmune neuroinflammation.

Example 3: Selective and Specific Targeting of Nanoparticle to Liver Sinusoidal Endothelial Cells In Vivo a) Nanoparticles were generated by first synthesizing iron oxide cores of about 11 nm according to (26) with 0.18 g FeOOH, 2.31 g oleic acid and 6.4 mL (5.0 g) 1-octadecene; the protocol was modified in interrupting the reaction after one hour for yielding larger core sizes of about 11 nm.

Then followed encapsulation of the cores according to (27) with some modifications: 2 mL of poly(maleic anhydride-alt-1-octadecene) solution (c=0.01 g/mL in CHCl$_3$) was added to a solution of 2 mg nanoparticles dissolved in 2 mL of chloroform and stirred at room temperature overnight. The solvent was then evaporated by exposure to a constant stream of $N_2$, and 2 mL of 20% TBE buffer were added. The solution was sonicated three times for 10 minutes, allowing the solution to cool in between. Subsequently, the solution was heated at 60° C. for 10 minutes. Forming aggregates were removed by centrifugation at 2400 g (three times for 10 minutes), and excess polymer was removed by ultracentrifugation (1 h, 50 000 g, 4° C.). Finally, the solution was filtered sequentially through filters with pore sizes of 0.45 μm, 0.2 μm and 0.1 μm. The quality of the particles was confirmed by size-exclusion-chromatography and transmission electron microscopy. The iron content was measured by treating 200 μL of a diluted sample with 50 μL of 5 M hydrochloric acid at 70° C. for 30 minutes (31). Thereafter, 150 μL of a 2 M acetate buffer (pH=4.8) containing 10% ascorbic acid was added to 50 μL of each sample, followed by 100 μL of a solution of 50 mg bathophenanthroline in 50 mL water. After, 15 minutes, the absorption was measured at 540 nm. The general design of the nanoparticles is illustrated in FIG. 3.

b) Comparative nanoparticles, nanosomes comprising a lipid bilayer, were generated by the procedure described in Bruns, et al., *Nat. Nanotechnol.* 2009, 4 193-201.

Results:

a) The obtained nanoparticles were injected into mice and, as assessed by MRI, found to specifically accumulate in the liver. Moreover, radioactive labelling of the cores with $^{59}$Fe showed that about 80% of the injected particles were retained in the liver. To confirm hepatotropism and further identify specific target cells, fluorescent semiconductor CdSe/ZnS cores' (quantum dots), as described in (32), were used as core instead of iron oxide, leaving the capsule and contact surface of the nanoparticles unchanged. Intravital microscopy was then performed after injection of these fluorescent nanoparticles into mice, showing that these nanoparticles rapidly accumulate predominantly in LSEC (FIG. 4A). A minor fraction of the injected nanoparticles was found in Kupffer cells or in some endothelial cells of intestinal veins that feed the portal vein.

The obtained nanoparticles of the invention were further injected into mice and found to accumulate in liver sinusoidal endothelial cells as assessed by transmission-electron microscopy (FIG. 4B).

b) For comparison, fluorescent nanosomes prepared according to Bruns et al., 2009, were injected into mice that two days before had been depleted of Kupffer cells through injection of chlodronate-containing liposomes (FIG. 4C: b) or not depleted of Kupffer cells through injection of sham liposomes (FIG. 4C: a). In sham-treated control mice, liposomes are internalized by Kupffer cells, as inferred from the characteristic staining pattern. In clodronate-treated mice, uptake of particles was substantially reduced, confirming that nanocrystals embedded into lipoproteins are indeed internalized by Kupffer cells. FIG. 4C shows that the nanosomes accumulate in Kupffer cells, but not in LSEC.

Example 4: Treatment of Experimental Neuroinflammation with Autoantigen-Loaded Nanoparticles In Vivo For covalent conjugation of neuroantigen peptide (encephalitogenic Act-9 peptide derived from the amino acid sequence of myelin basic protein), iron oxide-core nanoparticles were synthesized as described in example 3 and adjusted to a concentration of 6 μmol/L in 50 mM SBB-buffer (pH=9). An equal amount of 1-Ethyl-3-(3-dimethyl-aminopropyl)carbodiimide (c=60 nmol/L), dissolved in a 50 mM SBB-buffer (pH=9), was added. After 5 minutes, a 1000-fold excess of the neuroantigen peptide was added and the solution was incubated under rotation for 2 h at room temperature and then overnight at 4° C. On the next day, the solution was filtered under centrifugal force in a filter device (100 kDa, 2500 g, 4° C.) and the remnant resuspended in PBS. This procedure was repeated 20 times to remove all excess peptide. The obtained peptide-particle conjugates were dissolved in PBS and subjected to size-exclusion-chromatography to assure for the absence of free peptide. Then, the iron content was measured to determine the concentration of the peptide-particle suspension.

Results: The thus obtained peptide-loaded nanoparticles or, as control, unconjugated peptide-free nanoparticles were then injected into B10 μL mice (n=6), one day after induction of experimental autoimmune encephalomyelitis (EAE) by immunization to Ac1-9 myelin basic protein peptide (25). As shown in FIG. 5, only the neuropeptide-loaded nanoparticles induced complete protection from clinical EAE. In contrast, peptide-free nanoparticles did not protect from EAE and the mice developed clinical EAE scores that were similar to those of PBS-treated mice.

Example 5: T-Reg-Mediated Control of Autoimmunity by Nanoparticle-Based Antigen Delivery to Tolerogenic Liver Cells Liver dendritic cells (DC), liver sinusoidal endothelial cells (LSEC) and Kupffer cells (KC) are liver resident antigen-presenting cells constitutively expressing MHC II molecules and capable of stimulating CD4$^+$ T cells. To test whether these liver cells are involved in Treg induction, primary liver DC, LSEC or KC were used to stimulate CD4$^+$Foxp3$^-$ non-Treg cells from the spleen of (tg4× Foxp3gfp.KI) F1 mice. These non-Treg cells specifically recognize myelin basic protein (MBP), and allow monitoring of Treg conversion based on the Foxp3-linked expression of green fluorescent protein (GFP). The stimulation of non-Treg cells was performed in the presence of the specific MBP peptide and exogenous TGFβ, which is required for Treg conversion. All tested liver cell types were capable of inducing MBP-specific Foxp3$^+$ Tregs; however, LSEC were more efficient in inducing Tregs than KC and liver DC (FIG. 6A). The ability of the liver cells to provide TGFβ-signals in the absence of exogenous TGF was then tested. Liver DC and KC were not efficient in inducing Tregs (FIG. 6B), whereas LSEC could induce Treg conversion at increased rates (FIG. 6B). To confirm that LSEC can provide TGFβ-signals that promote Treg conversion, CD4$^+$CD25$^-$ non-Tregs from (hCD2-ΔkTβ RIIxtg4) F1 mice were stimulated on LSEC; these T cells carry a dominant-negative TGFβ type II receptor and thus display reduced sensitivity to TGFβ. The inventors found strongly reduced conversion rates of TGFβ-insensitive T cells to Foxp3$^+$ Tregs, as compared to wild-type T cells (FIG. 6C), indicating that the efficiency of LSEC to induce Tregs depends on TGFβ-signaling. Although LSEC seem to provide TGFβ-signals for Treg induction (FIG. 6B), active TGF in LSEC supernatants was not detected (not shown). Therefore, the inventors tested whether LSEC have bound TGFβ to their membrane; in complex with latency-associated peptide (LAP) (40, 41), TGFβ can be tethered to the surface of cells through glycoprotein-A repetitions predominant (GARP, also known as LRRC32) (42). Such membrane-bound TGFβ was shown to induce a tolerogenic phenotype and Foxp3-expression in stimulated T cells (41). Indeed, the inventors found by immunohistochemistry that GARP as well as LAP co-localized with CD3 LSEC (FIG. 6D), whereas. GARP and LAP expression was undetectable on other liver cells. Quantitation of GARP and LAP expression by flow cytometry confirmed cell surface expression of both GARP and LAP by LSEC, but not by splenic DC (FIG. 6E). These findings indicate that LSEC can efficiently induce antigen-specific Tregs through membrane-bound TGF-β.

Next, in vitro LSEC-induced MBP-specific Tregs were generated, and their suppressive functionality tested in vivo in a mouse model of multiple sclerosis, experimental autoimmune encephalomyelitis (EAE). Whereas the control group developed clinical EAE, mice that received LSEC-induced MBP-specific Tregs (FIG. 6F; T(LSEC)) were almost completely protected from MBP-induced EAE. However, this suppressive effect was limited to about three weeks, indicating that the transferred Tregs were not stable. The inventors reasoned that a more sustained Treg stability and protection from EAE could be achieved by antigen-specific Treg induction by LSEC in vivo.

To develop a method for selective delivery of autoantigen to LSEC in vivo, the inventors made use of nanoparticles (NP) that are rapidly cleared from the circulation through uptake by liver cells. Specifically, the inventors took advantage of a polymer-coated nanoparticle (43), which they observed to accumulate selectively in liver sinusoidal endothelium (data not shown). To generate an effective antigen carrier system, a simple one-step coupling strategy using a carbodiimide crosslinking approach was chosen to attach the MBP peptide to polymer-coated nanoparticles with superparamagnetic iron oxide core. Each nanoparticle was loaded maximally with 100 peptide molecules per nanoparticle as demonstrated by binding assays with $^{14}$C-radiolabeled MBP peptide (FIG. 10). Peptide-loading did not influence size, shape and charge of nanoparticles as determined by measurement of the Zeta potential, size exclusion chromatography and electron microscopy (FIG. 12). To investigate whether MBP peptide-loading altered pharmacokinetics and tropism of our nanoparticles, kinetic turnover studies with $^{14}$C-radiolabeled MBP peptide-nanoparticle conjugates ($^{14}$C-MBP—NP) were performed in comparison with $^{59}$Fe-radiolabeled nanoparticles conjugated to non-labeled MBP peptide (MBP—$^{59}$Fe—NP). Both radiolabels were cleared with similar kinetics (FIG. 7A), predominantly by the liver (FIG. 7B). Low amounts of radioactivity could be detected in spleen and kidney, whereas uptake into other organs was negligible. In addition, organ uptake was visualized by dynamic magnetic resonance imaging, revealing only hepatic targeting of both MBP peptide-loaded and unloaded nanoparticles (FIG. 7C, Table 1 (below)). Thus, MBP peptides are not excreted via the kidney, but transported by the desired targeting effect of the nanoparticles of the invention to liver cells.

To further investigate the cellular tropism of administered peptide-nanoparticle conjugates, conventional as well as intravital confocal fluorescence microscopy of the liver was performed, using nanoparticles with a fluorescent quantum dot core (44). Prior to administration of fluorescent MBP peptide-nanoparticle conjugates, recipient mice were injected with FITC-dextran that is rapidly absorbed by LSEC. After intravenous injection of MBP-nanoparticles or unloaded nanoparticles, the inventors observed a rapid accumulation of both, unloaded and MBP peptide-loaded nanoparticles in the liver, which clearly co-localized with FITC-dextran stained LSEC (FIG. 7D). To further confirm uptake of peptide-loaded and unloaded nanoparticles by LSEC, transmission electron microscopy of liver slides was performed, and a sizeable internalization of MBP peptide-nanoparticle conjugates in endosomal compartments of LSEC detected (FIG. 7E). To confirm that delivered peptide can be presented to T cells, Treg conversion in vitro by LSEC in the presence of free MBP peptide or of MBP peptide bound to nanoparticles (MBP—NP) was studied. The inventors found that Treg generation occurred with similar efficacy (FIG. 11), indicating that MBP peptide delivered by nanoparticles was efficiently presented to T cells. Together, these findings demonstrate that these nanoparticles, with or without peptide cargo, are selectively taken up by LSEC in vivo, and thus facilitate selective delivery of antigen peptides to LSEC.

in hCD2-ΔkTβRII mice (46), which feature TGFβ-insensitive T cells (FIG. 8D). Thus, it can be concluded that also in vivo, the efficacy of nanoparticle-mediated tolerance induction is dependent on TGF signaling to T cells. To confirm that nanoparticle-mediated protection from EAE was dependent on Treg function in vivo, Tregs were depleted in mice that had received MBP-nanoparticles by repeated administration of the PC61 antibody that recognizes CD25 (47) (FIG. 8E); the efficacy of depletion was confirmed by flow cytometry (FIG. 13). Although administration of MBP-nanoparticles induced protection from EAE in control mice, MBP-nanoparticles could not prevent the development of disease in Treg-depleted mice (FIG. 8E). In fact, the disease severity precipitated by Treg depletion was similar to the

TABLE 1

Detailed parameters of MRI-sequences used for in vivo animal measurements
Abbreviations: Fast Field Echo sequence (FFE), Field of View (FoV), excitation flip angle (FA), Repetition Time (TR), Echo Time (TE), Number of Signal Averages (NSA).
The measurements were done in the imaging-mode at 22° C. room temperature.

|  | FoV [mm] | matrix | slice thickness [mm] | effective voxel volume (μm)³ | slices | FA [°] | TR [ms] | TE [ms] | NSA | dynamic interval [s] | total scan time [min] |
|---|---|---|---|---|---|---|---|---|---|---|---|
| T2*-weighted coronal multisclice FFE | 100 × 35 | 448 | 1 | 223 × 223 × 1000 | 22 | 30 | 602 | 6.9 | 4 | N/A | 3:59 |
| T2*-weighted transverse multislice FFE | 35 × 35 | 288 | 1 | 208 × 208 × 1000 | 20 | 80 | 353 | 6.9 | 4 | N/A | 3:02 |
| T2*-weighted dynamic transverse FFE | 34 × 34 | 160 | 1.3 | 213 × 213 × 1100 | 1 | 20 | 29 | 6.9 | 8 | 1.42 | 17:16 |

The proposed immunosuppressive effect of MBP-nanoparticles in vivo was first tested in MBP-induced EAE in B10 μL mice (FIG. 8A). A single intravenous injection of MBP peptide-loaded nanoparticles one day after EAE-induction provoked a lasting and almost complete protection from clinical EAE; in contrast, control mice treated with PBS or with unloaded nanoparticles developed clinical EAE symptoms (FIG. 8A). Remarkably, even tg4 mice (45), which feature MBP-specific CD4⁺ T cells and develop more severe EAE, were protected from disease by a single MBP—NP injection one day after EAE-induction (FIG. 8B); control mice receiving an equivalent dose of free MBP peptide, in contrast, developed severe EAE (FIG. 8B). To confirm the efficacy of the inventive treatment approach in another independent disease model, the effect of nanoparticles loaded with myelin oligodendrocyte glycoprotein (MOG) peptides on the development of MOG-induced EAE was tested in C57BL/6 mice. Consistent with the inventors' observations in MBP-induced EAE of B10 μL mice, administration of MOG peptide-loaded nanoparticles to C57BL/6 mice one day after EAE induction lastingly rescued recipient mice from developing any clinical disease symptom; in contrast, control mice receiving unloaded nanoparticles developed EAE (FIG. 8C).

As the inventors have shown above that tolerance induction by LSEC required TGFβ signaling to T cells, they reasoned that nanoparticle-based targeting of autoantigen peptides to LSEC should be ineffective in mice with TGFβ-insensitive T cells. Indeed, MOG peptide-loaded nanoparticles induced only a minor degree of protection from EAE disease severity of the control group receiving PBS instead of MBP-nanoparticles (FIG. 8E), demonstrating that Tregs are critically involved in nanoparticle-mediated tolerance induction in vivo.

Having determined that autoantigen peptide-loaded NP efficiently prevented autoimmune disease development, the inventors addressed the even more important issue of whether peptide-loaded nanoparticles are an effective treatment of established autoimmune disease. Therefore, they first induced clinical EAE in C57BL/6 mice by MOG-immunization. At the time of treatment, both the recipients of MOG peptide-loaded nanoparticles and control mice showed manifest clinical symptoms with similar disease scores (FIG. 14). The control group progressed in EAE severity; in contrast, the mean clinical scores of MOG-NP treated mice improved rapidly and substantially (FIG. 9A, FIG. 9B). Of note, tolerance induced by a single therapeutic injection of MOG peptide-loaded nanoparticles continued throughout an extended follow-up period of 9 weeks (FIG. 9A, FIG. 9B). In conclusion, nanoparticle-mediated autoantigen delivery to LSEC is therapeutically effective in autoimmune disease.

Taken together, the inventors' results indicate that nanoparticle-based targeted delivery of autoantigen peptides to Treg-inducing LSEC in vivo can restore immune tolerance to self and serve the effective treatment of autoimmune disease. Therefore, this approach offers a solution to the problem of effectuating a Treg-based therapy for autoimmune disease by providing an efficient methodology for inducing antigen-specific Tregs in vivo. LSEC are particularly well-suited as target cells for tolerogenic antigen-delivery, since they induce T cell tolerance and do not support inflammatory T cell effector responses. Nanoparticles targeting splenic DC are also being explored as tools for antigen-specific tolerance induction. However, DC display a high degree of plasticity and readily can differentiate to inflammatory cells, whereas LSEC display a robust tolerance-inducing phenotype even in the presence of pro-inflammatory signals. Therefore, autoantigen delivery to robust tolerogenic LSEC provides increased safety, notably when attempting to treat individuals with on-going inflammation.

Nanoparticles are most commonly modified by the attachment of specific ligands to their surface in order to avoid their rapid clearance by the liver and to redirect them to specific targets, e.g. to cancer cells. Nevertheless, the targeting efficacy of such redirection is still limited by undesired uptake in the liver. By taking advantage of the highly selective nanoparticle uptake by LSEC, the inventive approach avoids mistargeting of autoantigen to potentially inflammatory cells. Indeed, this efficient and selective delivery to LSEC may explain the stable and potent treatment efficacy induced by only a single administration of peptide-loaded nanoparticles.

The inventors' data provide proof-of-principle that antigen-specific tolerance induction in vivo can be attained through nanoparticle-based antigen-delivery to LSEC. These findings enable the development of an effective Treg-based treatment for human autoimmune and inflammatory diseases in which the driving antigens have been identified.

REFERENCES

1. Hogquist, K. A., Baldwin, T. A., and Jameson, S. C. 2005. Central tolerance: learning self-control in the thymus. *Nat. Rev. Immunol.* 5: 772-782
2. Goodnow, C. C., Sprent, J., Fazekas de St Groth, B., and Vinuesa, C. G. 2005. Cellular and genetic mechanisms of self tolerance and autoimmunity. *Nature.* 435: 590-597.
3. Jonuleit, H., and Schmitt, E. 2003. The regulatory T cell family: distinct subsets and their interrelations. *J. Immunol.* 171: 6323-6327.
4. Cohen, I. R. 2001. *Tending Adam's garden: evolving the cognitive immune self.* Academic Press. New York, USA. 266 pp.
5. Viglietta, V., Baecher-Allan, C., Weiner, H. L., and Hafler, D. A. 2004. Loss of functional suppression by CD4+ CD25+ regulatory T cells in patients with multiple sclerosis. *J. Exp. Med.* 199: 971-979.
6. von Herrath, M. G., and Harrison, L. C. 2003. Antigen-induced regulatory T cells in autoimmunity. *Nat. Rev. Immunol.* 3: 223-32.
7. Fontenot, J. D., Gavin, M. A., and Rudensky, A. Y. 2003. Foxp3 programs the development and function of CD4+ CD25+ regulatory T cells. *Nat. Immunol.* 4: 330-336.
8. Sakaguchi, S. 2005. Naturally arising Foxp3-expressing CD25+CD4+ regulatory T cells in immunological tolerance to self and non-self. *Nat. Immunol.* 6: 345-352.
9. Wan, Y. Y., and Flavell, R. A. 2006. The roles for cytokines in the generation and maintenance of regulatory T cells. *Immunol. Rev.* 212: 114-130.
10. Huber, S., and Schramm, C. 2006. TGF-beta and CD4+ CD25+ regulatory T cells. *Front. Biosci.* 11: 1014-1023.
11. Shevach, E. M. 2009. Mechanisms of Foxp3+ T regulatory cell-mediated suppression. *Immunity* 30: 636-645.
12. Von Boehmer, H. 2005. Mechanisms of suppression by suppressor T cells. *Nat. Immunol.* 6: 338-344.
13. Gavin, M. A., Clarke, S. R., Negrou, E., Gallegos, A., and Rudensky, A. 2002. Homeostasis and anergy of CD4(+)CD25(+) suppressor T cells in vivo. *Nat. Immunol.* 3: 33-41.
14. Walker, L. S., Chodos, A., Eggena, M., Dooms, H., and Abbas, A. K. 2003. Antigen-dependent proliferation of CD4+CD25+ regulatory T cells in vivo. *J. Exp. Med.* 198: 249-258.
15. Liang, S., et al. 2005. Conversion of CD4+CD25− cells into CD4+CD25+ regulatory T cells in vivo requires B7 costimulation, but not the thymus. *J. Exp. Med.* 201: 127-137.
16. Knoechel, B., Lohr, J., Kahn, E., Bluestone, J. A., and Abbas, A. K. 2005. Sequential development of interleukin 2-dependent effector and regulatory T cells in response to endogenous systemic antigen. *J. Exp. Med.* 202: 1375-1386.
17. Kretschmer, K., et al. 2005. Inducing and expanding regulatory T cell populations by foreign antigen. *Nat. Immunol.* 6: 1219-1227.
18. Quintana, F. J., et al. 2008. Control of T(reg) and T(H)17 cell differentiation by the aryl hydrocarbon receptor. *Nature.* 453: 65-71.
19. Crispe, I. N. 2003. Hepatic T cells and liver tolerance. *Nat. Rev. Immunol.* 3: 51-62.
20. Limmer, A., et al. 1998. Failure to induce organ-specific autoimmunity by breaking of tolerance: importance of the microenvironment. *Eur. J. Immunol.* 28: 2395-2406.
21. Knolle, P. A., et al. 1999. Induction of cytokine production in naïve CD4 (+) T cells by antigen-presenting murine liver sinusoidal endothelial cells but failure to induce differentiation toward Th1 cells. *Gastroenterology* 116: 1428-1440.
22. Limmer, A., et al. 2000. Efficient presentation of exogenous antigen by liver endothelial cells to CD8+ T cells results in antigen-specific T cell tolerance. *Nat. Med.* 6: 1348-1354.
23. Caine, R. Y., et al. 1969. Induction of immunological tolerance by porcine liver allografts. *Nature* 223: 472-476.
24. Cantor, H. M., and Dumont, A. E. 1967. Hepatic suppression of sensitization to antigen absorbed into the portal system. *Nature* 215: 744-745.
25. Lath, S., et al. 2008. Ectopic expression of neural autoantigen in mouse liver suppresses experimental autoimmune neuroinflammation by inducing antigen-specific Tregs. *J. Clin. Invest.* 118: 3403-3410.
26. Yu, W. W., Falkner, J. C., Yavuz, C. T., and Colvin, V. L. 2004. Synthesis of monodisperse iron oxide nanocrystals by thermal decomposition of iron carboxylate salts. *Chem. Commun.* 20: 2306-2307.
27. Shtykova, E. V., et al. 2008. Hydrophilic monodisperse magnetic nanoparticles protected by an amphiphilic alternating copolymer, *J. Phys. Chem. C* 112: 16809-16817.
28. Wiegard, C., Frenzel, C., Herkel, J., Kallen, K. J., Schmitt, E., and Lohse, A. W. 2005. Murine liver antigen presenting cells control suppressor activity of CD4+ CD25+ regulatory T cells. *Hepatology* 42:193-199.
29. Schrage, A., et al. 2008. Murine CD146 is widely expressed on endothelial cells and is recognized by the monoclonal antibody ME-9F1. *Histochem. Cell. Biol.* 129:441-451.

30. Wiegard, C., et al. 2007. Defective T helper 1 response by hepatocyte-stimulated CD4 T cells impairs anti-viral CD8 response and viral clearance. *Gastroenterology* 133: 2010-2018.
31. Huberman, A., and Perez C. 2002. Nonheme irort determination. *Anal. Biochem.* 307: 375-378.
32. Wu, X. et al. 2002. Immunofluorescent labeling of cancer marker Her2 and other cellular targets with semiconductor quantum dots. *Nat. Biotechnol.* 21: 41-46.
33. Nguyen et al., 2004, Gene Ther. 11 (Suppl 1); S76-S84
34. Carambia et al. 2010, J. Hepatol 52, S59-S182.
35. Minchin 2008. Nature Nanotechnol. 3: 12-13.
36. Giri et al. 2011, Acta Biophys Sin, 1-7.
37. Shen et al. 2011, Int. J. Nanomedicine 6: 1229-1235.
38. Wu et al. Mol. Pharm. 6:1506-1517.
39. Bruns et al., Nat. Nanotechnol. 2009, 4:193-201:
40. H. L. Weiner, A. P. da Cunha, F. Quintana, H. Wu. *Immunol Rev* 241, 241-259 (2011).
41. J. Andersson, et al. *J Exp Med* 205, 1975-1981 (2008).
42. D. Q. Tran, et al. *Proc Natl Acad Sci USA* 106, 13445-13450 (2009).
43. T. Pellegrino, et al. *Nano Letters* 4, 703-707 (2004).
44. A. Bartelt, et al. *Nat Med* 17, 200-205 (2011).
45. G. Y. Liu, et al. *Immunity* 3, 407-415 (1995).
46. S. Huber, et al. *J Immunol* 173, 6526-6531 (2004).
47. J. Shimizu, S. Yamazaki, S. Sakaguchi. *J Immunol* 163, 5211-5218 (1999).

The invention claimed is:

1. A pharmaceutical composition comprising a nanoparticle, said nanoparticle being negatively charged and comprising:
   a) a micelle comprising an amphiphilic polymer rendering the nanoparticle water-soluble, wherein the polymer is a synthetic polymer selected from the group consisting of poly(maleic anhydride-alt-1-octa-decene), poly(maleic anhydride-alt-1-tetradecene), and polyisoprene-block poly-ethylene-oxide block copolymer, and
   b) a peptide comprising at least one T cell epitope associated with the outside of the micelle, wherein the peptide consists of 9 to 60 amino acids,
for use in generating regulatory T cells specific to said at least one T cell epitope in a subject, wherein said pharmaceutical composition is suitable for inducing in vivo generation of regulatory T cells specific for said at least one T cell epitope via uptake of said nanoparticle in liver sinusoidal endothelial cells and/or Kupffer cells and presentation of said epitope at the cell surface of said liver sinusoidal endothelial cells and/or Kupffer cells.

2. The pharmaceutical composition of claim 1, wherein the micelle does not comprise a solid core.

3. The pharmaceutical composition of claim 1, wherein the micelle coats a solid hydrophobic core.

4. The pharmaceutical composition of claim 3, wherein the core comprises a traceable inorganic material selected from the group consisting of iron oxide, CdSe/CdS/ZnS, silver and gold.

5. The pharmaceutical composition of claim 3, wherein the diameter of the core is 5 to 30 nm.

6. The pharmaceutical composition of claim 1, wherein the peptide is covalently linked to the micelle or non-covalently associated.

7. The pharmaceutical composition of claim 1, wherein the nanoparticle comprises a solid core comprising iron oxide having a diameter of about 9 to about 12 nm, which is encapsulated by a coating of poly(maleic anhydride-alt-1-octadecene) to which a peptide comprising a T cell epitope is covalently linked.

8. The pharmaceutical composition of claim 1, wherein the nanoparticles are suitable for transferring the peptide to liver sinusoidal endothelial cells of a subject in vivo.

9. The pharmaceutical composition of claim 1, wherein the nanoparticles are formulated for administration to a subject having a disease wherein suppression of a specific immune response is beneficial.

10. A method of treating a disease wherein suppression of a specific immune response is beneficial, comprising administering the pharmaceutical composition of claim 1, wherein said disease is selected from the group consisting of multiple sclerosis type I diabetes, rheumatoid arthritis, systemic lupus erythematosus, degeneration after trauma or stroke, graft versus host disease, transplant rejection, inflammatory bowel disease (IBD), asthma and allergy.

11. The pharmaceutical composition of claim 9, wherein the disease is selected from the group consisting of multiple sclerosis, type I diabetes, rheumatoid arthritis, systemic lupus erythematosus, degeneration after trauma or stroke, graft versus host disease, transplant rejection, inflammatory bowel disease (IBD), asthma and allergy.

12. The pharmaceutical composition of claim 3, wherein the diameter of the core is 9 to 12 nm.

13. The pharmaceutical composition of claim 1, wherein the polymer is poly(maleic anhydride-alt-1-octadecene).

14. The pharmaceutical composition of claim 1, said peptide comprising several epitopes.

15. The pharmaceutical composition of claim 1, wherein said peptide comprises a combination of epitopes from different antigens.

16. The pharmaceutical composition of claim 1, wherein said epitope is presented via Major Histocompatibility Complex molecules of said liver sinusoidal endothelial cells and/or Kupffer cells, thereby inducing in vivo generation of said regulatory T cells specific for said at least one T cell epitope.

* * * * *